(12) United States Patent
Wilson et al.

(10) Patent No.: US 12,230,397 B2
(45) Date of Patent: Feb. 18, 2025

(54) ASSESSMENT OF ENDOTHELIAL CELLS AND CORNEAS AT RISK FROM OPHTHALMOLOGICAL IMAGES

(71) Applicant: Case Western Reserve University, Cleveland, OH (US)

(72) Inventors: David L. Wilson, Cleveland Heights, OH (US); Hao Wu, Cleveland Heights, OH (US); Naomi Joseph, Cleveland, OH (US); Chaitanya Kolluru, Cleveland Heights, OH (US); Beth Benetz, Cleveland, OH (US); Jonathan Lass, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 829 days.

(21) Appl. No.: 16/908,059

(22) Filed: Jun. 22, 2020

(65) Prior Publication Data
US 2021/0052157 A1    Feb. 25, 2021

Related U.S. Application Data

(60) Provisional application No. 62/889,750, filed on Aug. 21, 2019.

(51) Int. Cl.
*G16H 50/20*    (2018.01)
*A61B 3/00*    (2006.01)
(Continued)

(52) U.S. Cl.
CPC ........... *G16H 50/20* (2018.01); *A61B 3/0025* (2013.01); *A61B 5/4848* (2013.01);
(Continued)

(58) Field of Classification Search
CPC ......... G16H 50/20; G06T 7/11; G06T 7/0012; G06T 2207/10056; G06T 2207/20081;
(Continued)

(56) References Cited

U.S. PATENT DOCUMENTS

2018/0096742 A1*  4/2018  Donovan ............... G16H 50/30
2020/0035362 A1*  1/2020  Abou Shousha ...... G16H 50/70
(Continued)

OTHER PUBLICATIONS

Abou et al. "Segmentation of Corneal Endothelium Images Using a U-Net-based Convolutional Neural Network" (Year: 2018).*
(Continued)

*Primary Examiner* — Vu Le
*Assistant Examiner* — Winta Gebreslassie
(74) *Attorney, Agent, or Firm* — Eschweiler & Potashnik, LLC

(57) ABSTRACT

Embodiments discussed herein facilitate determining a prognosis for keratoplasty based on segmented endothelial cells. One example embodiment comprises a computer-readable medium storing computer-executable instructions that, when executed, cause a processor to perform operations, comprising: accessing an optical microscopy image comprising a set of corneal endothelial cells of a patient of a keratoplasty; segmenting, based at least in part on a first model, a plurality of corneal endothelial cells of the set of corneal endothelial cells; calculating one or more features based on the segmented plurality of corneal endothelial cells; and generating, via a second model trained based at least on the one or more features, a prognosis associated with the keratoplasty.

24 Claims, 28 Drawing Sheets

(51) Int. Cl.
    A61B 5/00      (2006.01)
    G06N 3/02      (2006.01)
    G06N 7/01      (2023.01)
    G06N 20/10     (2019.01)
    G06N 20/20     (2019.01)
    G06T 7/00      (2017.01)
    G06T 7/11      (2017.01)
(52) U.S. Cl.
    CPC ............ *A61B 5/7264* (2013.01); *G06N 3/02* (2013.01); *G06N 7/01* (2023.01); *G06N 20/10* (2019.01); *G06N 20/20* (2019.01); *G06T 7/0012* (2013.01); *G06T 7/11* (2017.01); *G06T 2207/10056* (2013.01); *G06T 2207/20081* (2013.01); *G06T 2207/20084* (2013.01); *G06T 2207/30024* (2013.01); *G06T 2207/30041* (2013.01)
(58) Field of Classification Search
    CPC . G06T 2207/20084; G06T 2207/30024; G06T 2207/30041; G06N 20/20; G06N 20/10; G06N 7/01; G06N 3/02; A61B 3/0025; A61B 5/4848; A61B 5/7264
    See application file for complete search history.

(56) References Cited

U.S. PATENT DOCUMENTS

| 2020/0302607 | A1* | 9/2020 | Canavesi ............ G06V 10/764 |
| 2021/0046124 | A1* | 2/2021 | Kinoshita ............ A61K 35/30 |

OTHER PUBLICATIONS

Adam et al. "Influence of applied corneal endothelium image segmentation techniques on the clinical parameters" (Year: 2016).*

Beth et al. "Endothelial Morphometric Measures to Predict Endothelial Graft Failure After Penetrating Keratoplasty" (Year: 2013).*

Benetz et al. "Endothelial Morphometric Measures to Predict Endothelial Graft Failure After Penetrating Keratoplasty." JAMA Ophthalmol. 2013;131(5):601-608, published Mar. 14, 2013.

Daniel et al. "Automated Segmentation of the Corneal Endothelium in a Large Set of 'Real-World' Specular Microscopy Images Using the U-Net Architecture." Scientific Reports, (2019) 9:4752, published on Mar. 18, 2019.

Fabija'nska, Anna. "Segmentation of Corneal Endothelium Images Using a U-Net-Based Convolutional Neural Network." Artificial Intelligence in Medicine 88 (2018) 1-13, published on Apr. 10, 2018.

Lass et al. "Endothelial Cell Density to Predict Endothelial Graft Failure After Penetrating Keratoplasty." ARCH OPHTHALMOL/ vol. 128 (No. 1), Jan. 2010, published Jan. 2010.

McCarey et al. "Review of Corneal Endothelial Specular Microscopy for FDA Clinical Trials of Refractive Procedures, Surgical Devices and New Intraocular Drugs and Solutions." Cornea. Jan. 2008 ; 27(1): 1-16, published Jan. 2008.

Monnereau et al. "Endothelial Cell Changes as an Indicator for Upcoming Allograft Rejection Following Descemet Membrane Endothelial Keratoplasty." American Journal of Ophthalmology, vol. 158, Issue 3, p. 485-495, published Sep. 1, 2014.

Patel et al. "Post-Operative Endothelial Cell Density is Associated with Late Endothelial Graft Failure After Descemet Stripping Automated Endothelial Keratoplasty." Ophthalmology (2019), published Feb. 11, 2019.

Ronneberger et al. "U-Net: Convolutional Networks for Biomedical Image Segmentation." MICCAI 2015, Cornell University, published on May 18, 2015.

Sayegh et al. "Cornea: Fundamentals, Diagnosis, and Management 4th Edition: Part II, Section 3, Examining and Imaging the Cornea and External Eye, Chapter 14: Specular Microscopy." ISBN 9780323357586. Published Sep. 23, 2016.

Vigueras-Guillén et al. "Fully Convolutional Architecture vs. Sliding-Window CNN for Corneal Endothelium Cell Segmentation." BMC Biomedical Engineering, vol. 1, Article No. 4 (2019), published Jan. 30, 2019.

* cited by examiner

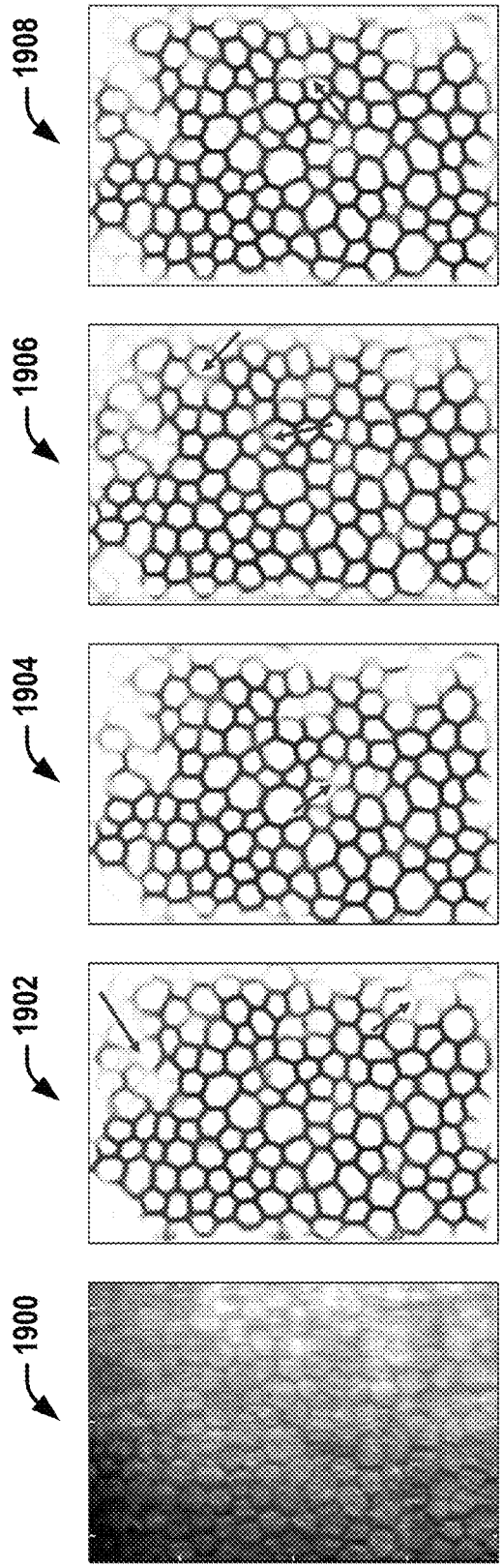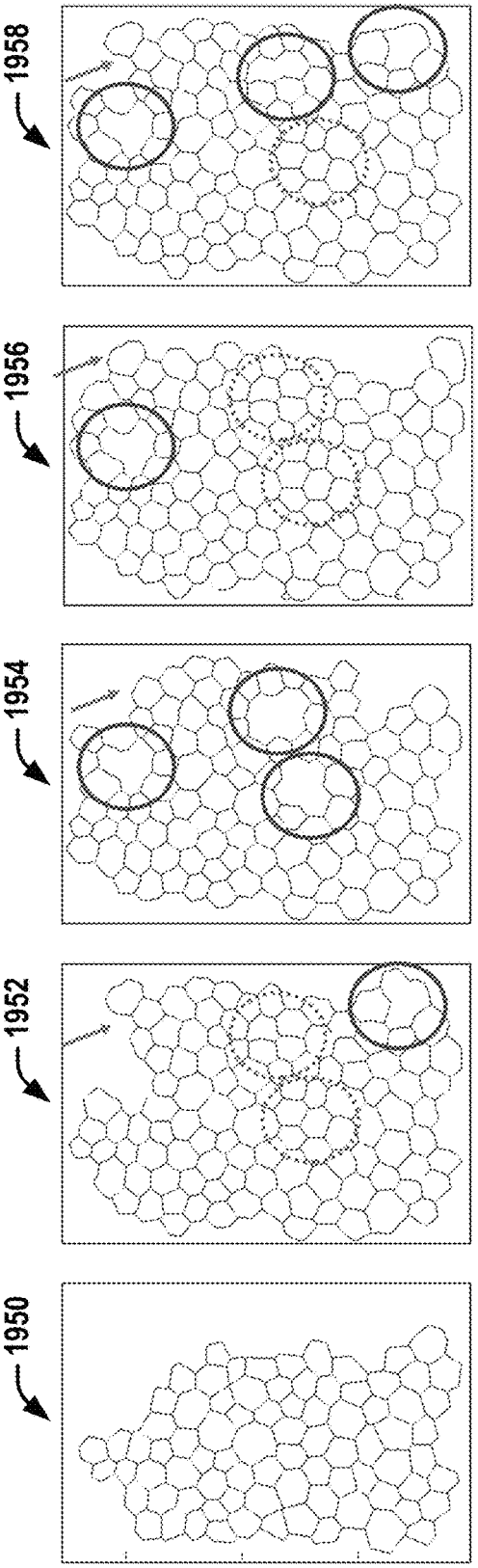
FIG. 19A
FIG. 19B

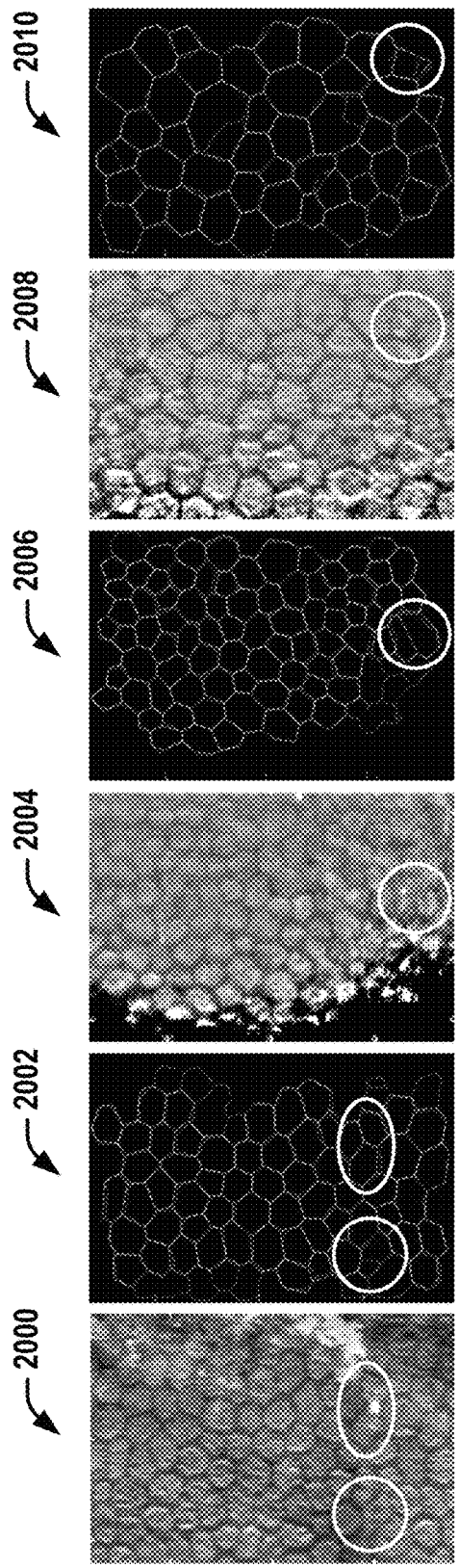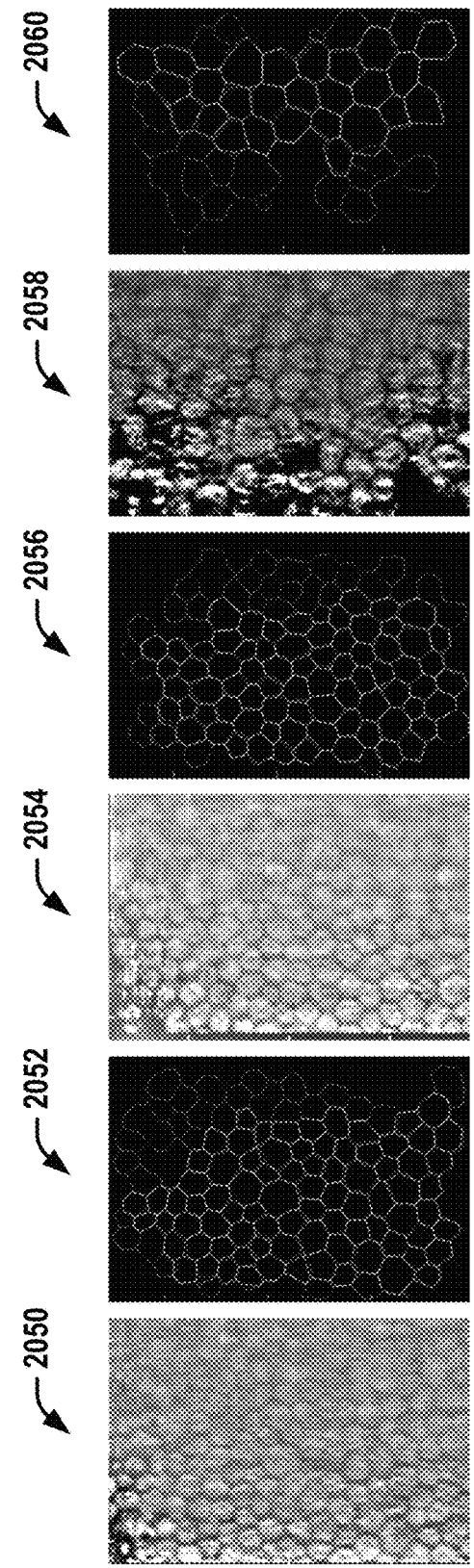
FIG. 20A
FIG. 20B

ASSESSMENT OF ENDOTHELIAL CELLS AND CORNEAS AT RISK FROM OPHTHALMOLOGICAL IMAGES

CROSS REFERENCE TO RELATED APPLICATIONS

This application claims the benefit of U.S. Provisional Patent Application No. 62/889,750 filed Aug. 21, 2019, entitled "ASSESSMENT OF ENDOTHELIAL CELLS AND CORNEAS AT RISK FROM OPHTHALMOLOGICAL IMAGES", the contents of which are herein incorporated by reference in their entirety.

FEDERAL FUNDING NOTICE

This invention was made with government support under the grant(s) EY029498 awarded by the National Institutes of Health. The government has certain rights in the invention.

BACKGROUND

The Eye Bank Association of America (EBAA) reported 48,366, corneal keratoplasties performed in the US in 2017, with 28,993 endothelial keratoplasties (EK) and 18,346 penetrating keratoplasty (PK) procedures. The regraft rate for 2016 was 8.8% for EK and 11.8% for PK, where graft failure involves regrafting for any reason or a cornea which remains cloudy without clearing for at least 90 days of observation.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 19A illustrates images of deep learning probability maps of an example test image following four types of pre-processing, in connection with various aspects discussed herein.

FIG. 19B illustrates images showing the final segmentation results of the EC image of FIG. 20 with the four pre-processing methods discussed above, according to various aspects discussed herein.

FIG. 20A illustrates three example EC images and corresponding segmentation highlighting cells with differences between manual and automatic segmentations, in connection with various aspects discussed herein.

FIG. 20B illustrates three examples of EC images showing the automatic segmentation method identifying and segmenting cells outside of the sample area of the ground truth annotations, in connection with various aspects discussed herein.

DETAILED DESCRIPTION

Figure 1:
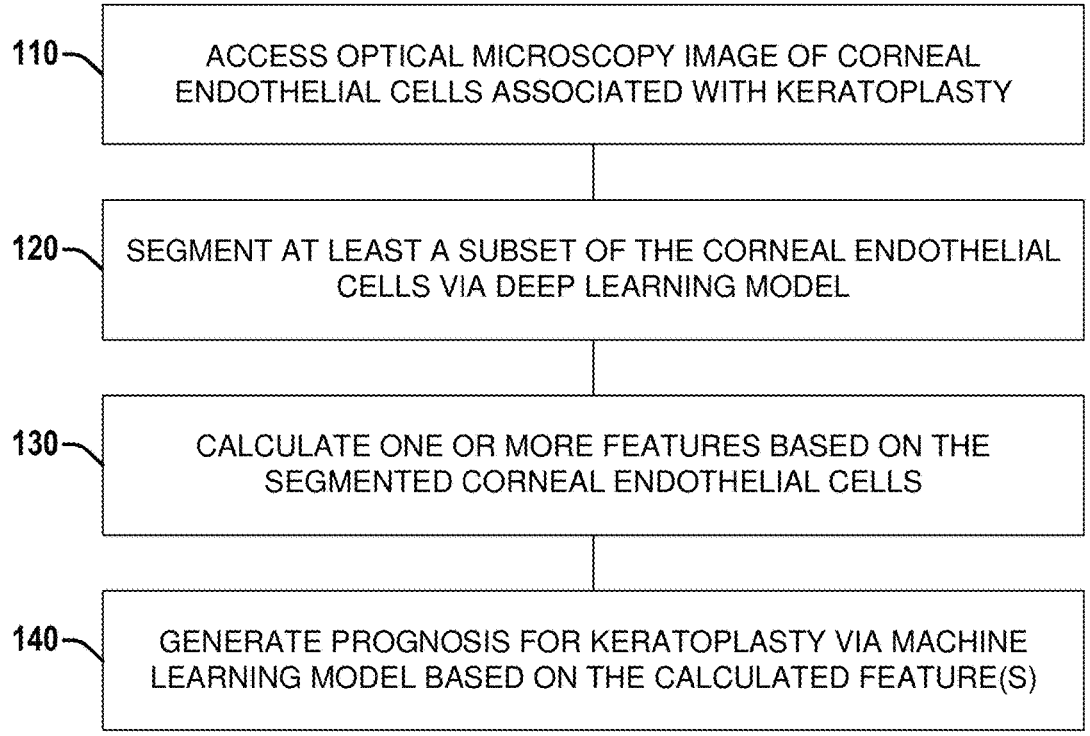
FIG. 1 illustrates a flow diagram of an example method/set of operations that can be performed by one or more processors to determine a prognosis for a keratoplasty based on features calculated from segmented corneal endothelial cells, according to various aspects discussed herein.

In light of the risks of graft failure via rejection or otherwise, successful predictive image analytics of potential failure can be advantageous. Via increased surveillance, patients can be identified for tailoring topical corticosteroid usage associated with some glaucoma risk, and counseling can be intensified to improve patient compliance. Compliance with medication is an issue with corneal grafts, and it is likely that interventions could improve results in a manner similar to the well-studied effect in glaucoma. Saving the initial graft is quite important, as there is a significant increase in rejection rate in a second graft, with mechanisms identified in mouse studies. By identifying possible rejection at a subclinical level, this could potentially reduce graft rejection failures significantly. Various embodiments can facilitate the identification of potential rejection and/or graft failure, which can reduce health care costs, patient discomfort, patient angst, and vision loss.

Evidence suggests that corneal EC images could predict graft rejection and failure. The corneal endothelium plays a critical role in maintaining stromal clarity. A sufficient number of endothelial cells, serving as Na+/K+-ATPase pump sites, are required to prevent corneal swelling which impairs vision and can ultimately lead to graft failure. The normal endothelial cell layer has a regular hexagonal structure (nature's preferred cellular arrangement, as described below). The literature suggests that changes in morphometric measures, including coefficient of variation (CV) of cell area (polymegathism) and the percentage of hexagonal cells or hexagonality (HEX), reflecting variation in cell shape (pleomorphism), may be more sensitive than endothelial cell density (ECD) in assessing endothelial health and dysfunction. Research performed in connection with various embodiments based on the National Eye Institute-sponsored Specular Microscopy Ancillary Study (SMAS) images found that 6-month HEX results were suggestive of an association with subsequent late graft failure, whereas CV was not predictive of graft failure. Consultants, Drs. Baydoun and Melles of the Netherlands Institute for Innovative Ocular Surgery (NIIOS), created a scoring system predictive of corneal rejection after Descemet Membrane Endothelial Keratoplasty (DMEK) surgery. In addition to CV and HEX, they described visual subjective scoring related to the cell morphology pattern and distribution, cellular reflectivity, presence/size of cell nuclei and appearance of cellular activation. Scoring metrics were determined by comparing rejection and non-rejection image groups, a process systematized in connection with various embodiments and the example use case discussed below.

Various embodiments discussed herein can comprise and/or employ techniques that can facilitate analyzing the images of cornea endothelial cells and determining of the degradation of these important cells maintaining corneal clarity. Some example embodiments comprise and/or employ image analytics software for prediction of keratoplasty failure from corneal EC images. These techniques can be employed to determine corneas at risk of rejection and failure (e.g., rejection or non-rejection failure), especially for transplanted corneal tissues. Embodiments can employ these highly automated techniques to enable routine, sophisticated analysis of ECs and corneas at risk. Various embodiments can be applied to corneal endothelial cells images acquired with various types of specular and confocal microscopes.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of an example method/set of operations 100 that can be performed by one or more processors to determine a prognosis for a keratoplasty based on features calculated from segmented corneal endothelial cells, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing an optical microscopy image of corneal endothelial cells of a keratoplasty patient. In various embodiments and in the example use case discussed below, the image can be obtained via a system and/or apparatus implementing the set of operations 100, or can be obtained from a separate medical imaging system (e.g., specular or confocal microscope, etc.). Additionally, the image can be accessed contemporaneously with or at any point prior to performing the set of operations 100.

The set of operations 100 can further comprise, at 120, segmenting at least a subset of the corneal endothelial cells of the image via a deep learning model, according to techniques discussed herein. For example, segmenting the corneal endothelial cells can comprise preprocessing the image, generating an output probability image via the deep learning model, generating a binarized output via thresholding, and thinning cell boundaries, each of which can be according to techniques discussed herein.

The set of operations 100 can further comprise, at 130, calculating one or more features associated with the segmented endothelial cells. The one or more features can comprise existing measures (e.g., endothelial cell density (ECD), coefficient of variation (CV) of cell area, hexagonality (HEX), etc.), one or more graph features (e.g., local or global graph features of any of the types discussed herein, etc.), or one or more other features discussed herein, including novel features introduced herein.

The set of operations 100 can further comprise, at 140, generating a prognosis for the keratoplasty (e.g., of rejection, failure or non-failure; of one of no adverse outcome, non-rejection failure, or rejection; etc.) based on the one or more calculated features via a trained model (e.g., a machine learning (ML) model such as a Linear Discriminant Analysis (LDA) classifier, a Quadratic Discriminant Analysis (QDA) classifier, a Support Vector Machine (SVM) classifier, or a Random Forest (RF) classifier, etc., another type of model, etc.).

Additionally or alternatively, set of operations 100 can comprise one or more other actions discussed herein in connection with determining a prognosis for keratoplasty based at least in part on features calculated from segmented endothelial cells.

Figure 2:
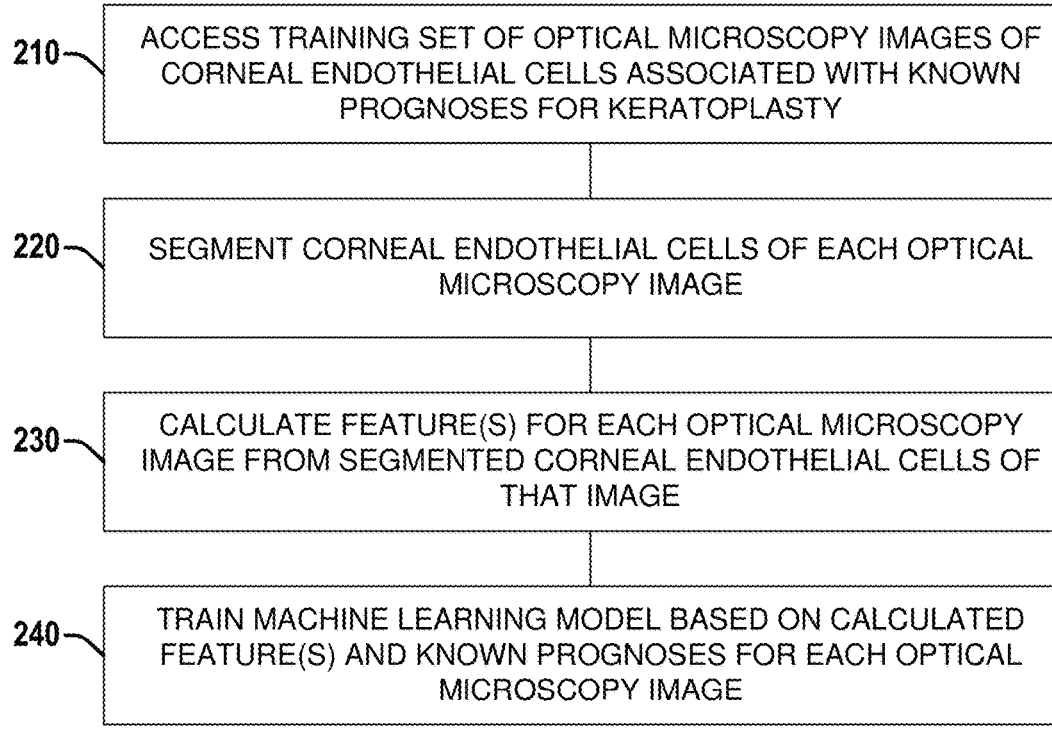
FIG. 2 illustrates a flow diagram of an example method/set of operations that can be performed by one or more processors to train a model to prognosis for a keratoplasty based on features calculated from segmented corneal endothelial cells, according to various aspects discussed herein.

Referring to FIG. 2, illustrated is a flow diagram of an example method/set of operations 200 that can be performed by one or more processors to train a model to prognosis for a keratoplasty based on features calculated from segmented corneal endothelial cells, according to various aspects discussed herein.

The set of operations 200 can comprise, at 210, accessing a training set of optical microscopy images of corneal endothelial cells of a keratoplasty patients, wherein each optical microscopy image can be associated with a known prognosis (e.g., no adverse event vs. failure, no adverse event vs. non-failure rejection vs. rejection, etc.). In various embodiments and in the example use case discussed below, the training set of images can be obtained via a system and/or apparatus implementing the set of operations 200, or can be obtained from a separate medical imaging system. Additionally, the training set of images can be accessed contemporaneously with or at any point prior to performing the set of operations 200.

The set of operations 200 can further comprise, at 220, for each image of the training set, segmenting at least a subset of the corneal endothelial cells of the image via a deep learning model, according to techniques discussed herein. For example, segmenting the corneal endothelial cells can comprise pre-processing the image, generating an output probability image via the deep learning model, generating a binarized output via thresholding, and thinning cell boundaries, each of which can be according to techniques discussed herein.

The set of operations 200 can further comprise, at 230, for each image of the training set, calculating one or more features associated with the segmented endothelial cells. The one or more features can comprise existing measures (e.g., endothelial cell density (ECD), coefficient of variation (CV) of cell area, hexagonality (HEX), etc.), one or more graph features (e.g., local or global graph features of any of the types discussed herein, etc.), or one or more other features discussed herein, including novel features introduced herein.

The set of operations 200 can further comprise, at 240, based on the calculated features and the known prognoses, training a model (e.g., a machine learning (ML) model such as a Linear Discriminant Analysis (LDA) classifier, a Quadratic Discriminant Analysis (QDA) classifier, a Support Vector Machine (SVM) classifier, or a Random Forest (RF) classifier, etc., a deep learning model, etc.) to generate prognoses for keratoplasty based on features calculated from segmented endothelial cells.

Additionally or alternatively, set of operations 200 can comprise one or more other actions discussed herein in connection with constructing a model to determine a prognosis for keratoplasty based at least in part on features calculated from segmented endothelial cells.

Figure 3:
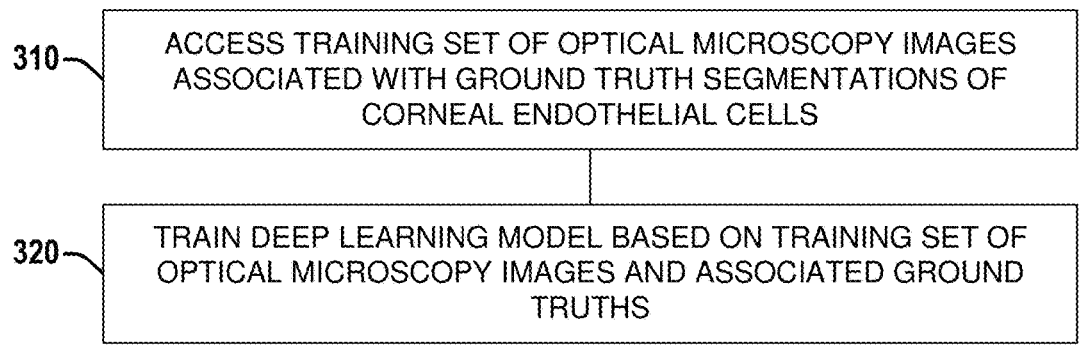
FIG. 3 illustrates a flow diagram of an example method/set of operations that can be performed by one or more processors to train a model via deep learning to segment endothelial cells, according to various aspects discussed herein.

Referring to FIG. 3, illustrated is a flow diagram of an example method/set of operations 300 that can be performed by one or more processors to train a model via deep learning to segment endothelial cells, according to various aspects discussed herein.

The set of operations 300 can comprise, at 310, accessing a training set of optical microscopy images of corneal endothelial cells, wherein each image can be associated with a ground truth segmentation of its endothelial cells. In various embodiments and in the example use case discussed below, the images can be obtained via a system and/or apparatus implementing the set of operations 300, or can be obtained from a separate medical imaging system. Additionally, the images can be accessed contemporaneously with or at any point prior to performing the set of operations 300.

The set of operations 300 can further comprise, at 320, training a model via deep learning based on the training set of images and the associated ground truth segmentations of the endothelial cells of each image of the training set. In various embodiments, the segmentation can be based on images that have been pre-processed according to various techniques discussed herein.

Additionally or alternatively, set of operations 300 can comprise one or more other actions discussed herein in connection with training a model via deep learning to segment endothelial cells.

Additional aspects and embodiments are discussed below in connection with the following example use case.

Example Use Case: Assessment of Endothelial Cells and Corneas at Risk from Ophthalmological Images The following discussion provides example embodiments in connection with an example use case involving analyzing the images of cornea endothelial cells and determination of the degradation of these important cells maintaining corneal clarity.

1. Overview

Review of CWRU's NIH-funded Cornea Donor Study (CDS) with the attached Specular Microscopy Ancillary Study (SMAS) and the Cornea Preservation Time Study (CPTS). The example use case was developed based on enhanced understanding, obtained from the CDS, of many factors surrounding the success of penetrating keratoplasty (PK) for conditions with endothelial dysfunction, notably Fuchs dystrophy and pseudophakic/aphakic corneal edema. In the associated SMAS, endothelial cell loss (ECL) was assessed in a subset of participants to examine its relationship with donor age. A slight association between increasing donor age and greater post-PKP corneal endothelial cell loss by 5 years was found among eyes whose grafts were successful at 5 years. Endothelial Cell Density (ECD) at 6 months, 1 year and 5 years was strongly predictive with subsequent graft failure. The CPTS data provides important information related to ECL following Descemet stripping automated endothelial keratoplasty (DSAEK) at three years related to storage time as well as the impact of donor, recipient, surgical and post-surgical factors on graft success and EC health. Since the literature suggests that changes in morphometrics (coefficient of variation (CV) of cell area and percentage of hexagonal cells or hexagonality (HEX)) may be more sensitive than ECD in assessing endothelial health and dysfunction, this was examined in connection with the example use case in a case-comparison group study from a subset of SMAS participants. It was found that 6-month HEX results suggested an association with subsequent graft failure, whereas CV was not predictive of graft failure. The example use case examined image analytics, as a more sensitive predictor of graft failure.

Review of image processing solutions. Recent papers demonstrate approaches in computerized image analysis of EC images as obtained from specular microscopes and, less commonly, confocal microscopes. There is opportunity for improved software. High-quality images in publications lead to concern about performance in clinical practice. Some recent papers use uncommon confocal rather than specular microscopy. Several reports describe limited performance of commercial systems clinically, suggesting a need for improvement. Nearly the entire focus has been on ECD, CV, and HEX, suggesting an opportunity to uncover new, important morphological and cell disarray image attributes, such as those discussed herein. Moreover, no quantitative paper has investigated image attributes associated with keratoplasty rejection.

Opportunity with machine learning. There are many success stories showing the ability of medical image analytics to predict clinical outcomes in cancer, Alzheimer's, and more. There has been particular success when applying image analytics to histology. In head-to-head comparisons, some studies show that image analytics can outperform physician experts, for example, at prediction of brain tumor recurrence, in a study from the Case Western Reserve University (CWRU) Center of Computational Imaging and Personalized Diagnostics (CCIPD). Given the linkage between EC images and cornea health, reports on EC quantitative biomarkers, and promise of machine learning, it is likely that image analytics will predict keratoplasty failures much better than current strategies.

Data. The quality and quantity of aggregated data allowed for high quality machine learning solutions to be created in connection with the example use case. The data sources included the following. SMAS (EY12728, EY012358) over a 10-year observation window includes 609 subjects with 105 failures with 8 imaging time points (6 mo, 1 Y, 2 Y, 3 Y, 4 Y, 5 Y, 7/8 Y, and 10 Y), each with 3 image repeats, giving 14,616 total images (2,520 failure images), minus drop out or deceased individuals. CPTS (EY020798) includes 1330 eyes at 5 time points (baseline, 6 months, 1, 2 and 3 years), each with 3 image repeats. Assuming a 10% failure rate, there are 15,960 total images (1,596 failure images). CNIIOS will consist of at least 50 failures and 100 matching no-failures, at about 6 time points with 3 repeats. This gives 2,700 total images (900 failure images). Altogether, the data comprises 31,476 total images with about 5,016 images from eyes with a graft failure. For the example use case, focusing on the predictive value of 6 month images, there were an estimated 6,267 images with 864 images from eyes with eventual graft failure. These images are all well-curated, manually analyzed images.

Advantages. As demonstrated by the example use case, various embodiments can detect keratoplasties at risk of failing and/or rejection, leading to early interventions that would reduce failures and/or rejections. Saving the initial keratoplasty is quite important, as there is a greater rejection rate in a second keratoplasty. Embodiments can provide multiple advantages, including reduced health care costs, patient discomfort, patient angst, and vision loss. Various embodiments can employ techniques discussed herein using specular (and/or confocal) microscopic images and image analytics to predict corneas at risk. The example use case and various embodiments also introduce novel concepts and approaches to keratoplasty rejection and failure prediction. Various embodiments can use powerful image analytics approaches to predict corneal grafts at risk. Computational features employed can comprise graph analytics approaches that improve upon current HEX measures by assessing disarray both between neighboring cells and cells in the more distant surrounding area. Other features can objectively evaluate attributes identified by the NIIOS group in their visual scoring system for predicting early rejection.

Motivation for image analytics approach. Normal EC images are comprised of compact, very regular hexagonal arrays of cells. In nature, the hexagonal structure is preferred to other ones that provide perfect coverage with thin membranes (only squares and triangles), because the hexagonal structure maximizes the area per cell while minimizing the number of cells required to provide coverage, and minimizes length of contact to create the "least interface energy". Hence, there is a substantive history of computing quantitative biomarkers (e.g., ECD and HEX) to assess cornea health. The example use case studied graph analytics that capture the full expression of structural disarray in non-normal EC images. Previously, many have described other EC image attributes, e.g., intracellular dark circles corresponding to nuclei, intracellular bright punctate corresponding to pigment deposits, intracellular dark structures corresponding to vacuoles, and dark structures at cell intersections corresponding to invading white blood cells. Consultants Baydoun and Melles implicated visual attributes with keratoplasty rejection by visually comparing images from eyes with and without rejection. The example use case computed a number of morphometric and intensity-based image features that capture the essence of these attributes and more. The features analyzed in the example use case provide very rich inputs from images that would be very difficult for a person, but easy for a computer, to compare between sets of failure and no-failure images. Results obtained in connection with the example use case show that these features can distinguish normal and abnormal EC images.

2. Techniques

The example use case comprised several different techniques. To enable routine, objective evaluation of corneas at risk, processing can be either fully automated or highly automated. The techniques employed in the example use case comprise: (1) Segmentation of endothelial cells; (2) Determination of classic EC metrics; (3) Determination of cellular features; and (4) Determination of corneas at risk. Each of these techniques is described in greater detail below.

Figure 4:
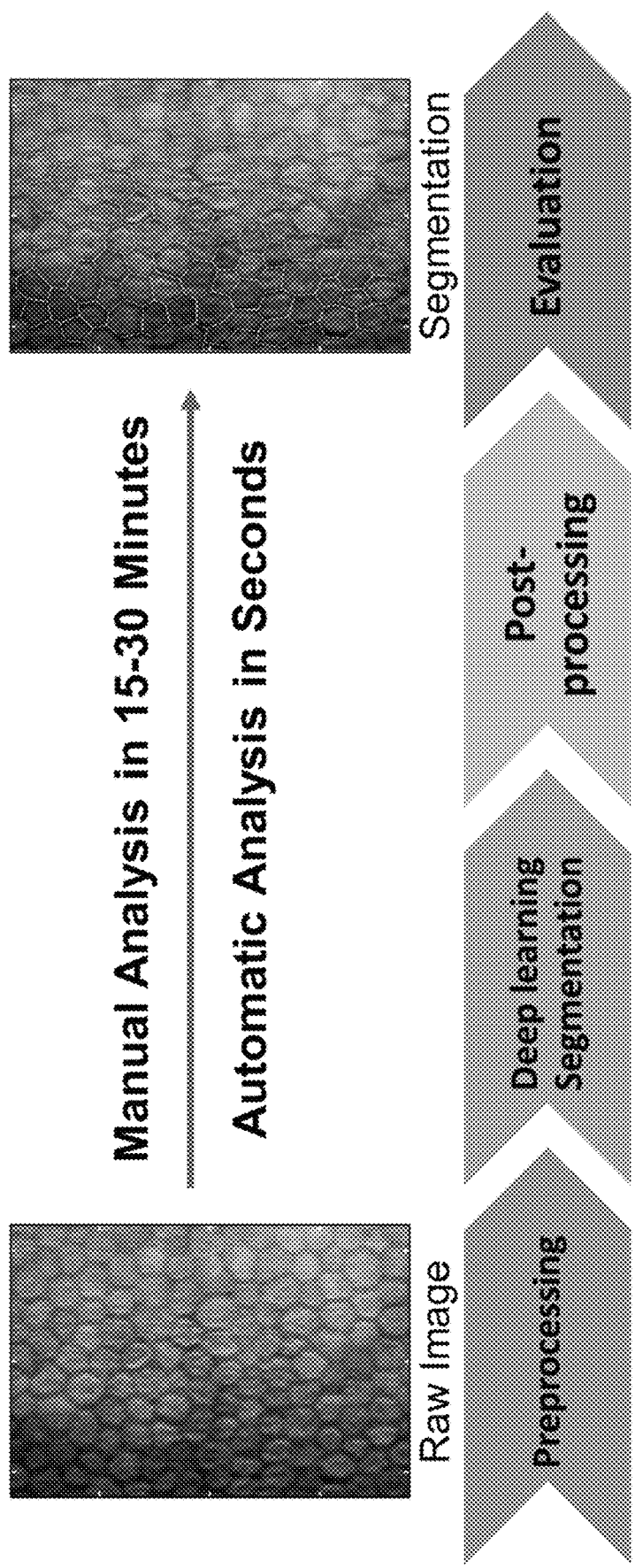
FIG. 4 illustrates a time comparison overview of the manual and automated techniques employed to segment an initial and raw endothelial cell image along with the flow diagram of the implemented automatic segmentation algorithm, in connection with various aspects discussed herein.

Referring to FIG. 4, illustrated is an overview of the techniques employed in the example use case, along with an initial and endothelial cell segmented version of an example EC image, in connection with various aspects discussed herein. When segmenting EC images, a cell-border was defined for the example use case as a collection of curve segments enclosing a bright cell. Manual segmentation of an image might take 15-30 minutes. Automatic analysis according to aspects discussed herein can reduce this time to seconds.

Figure 5:
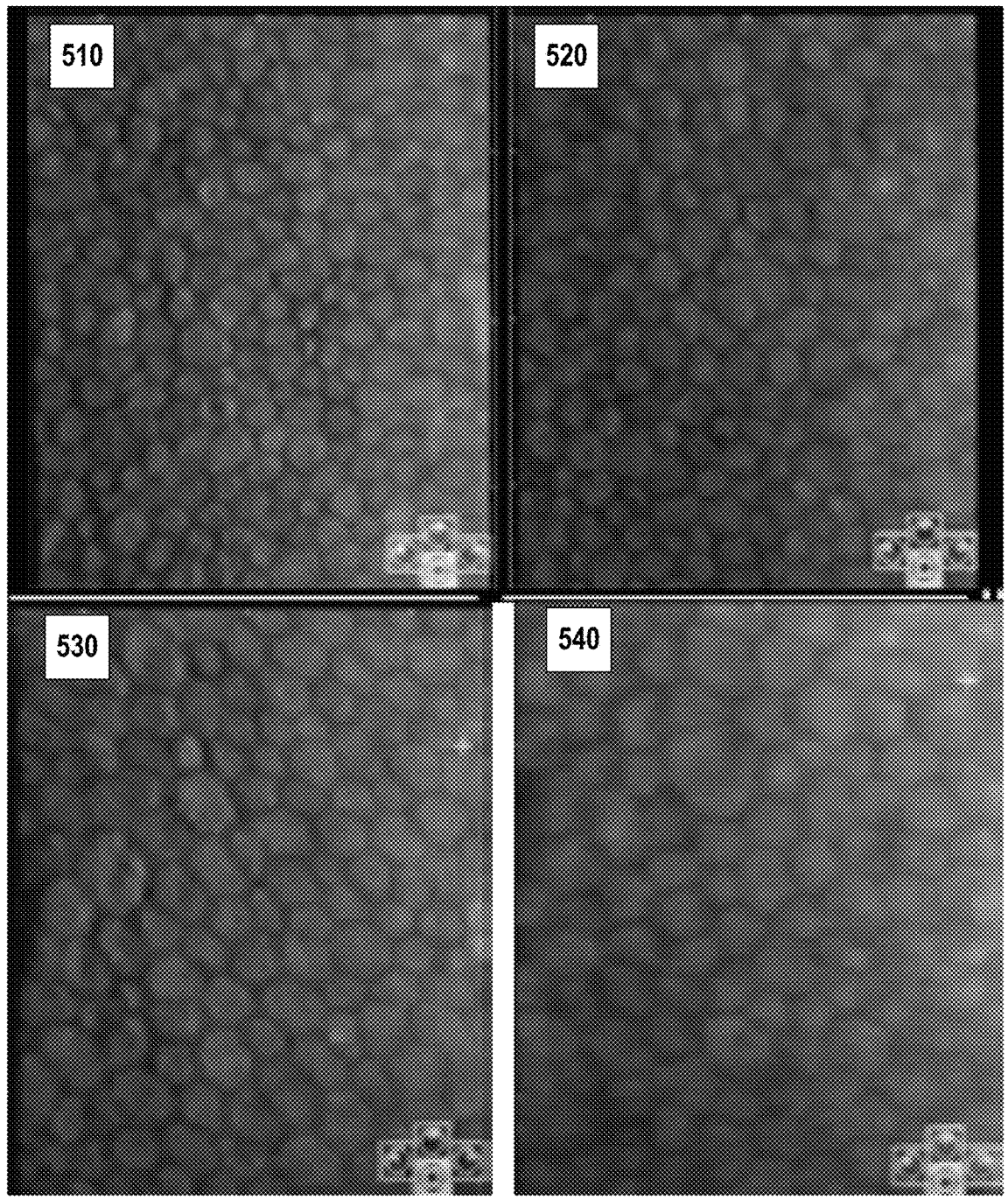
FIG. 5 illustrates serial specular microscope imaging following a penetrating keratoplasty (PK) procedure showing a continuing decrease in endothelial cell density, in connection with various aspects discussed herein.
Figure 6:
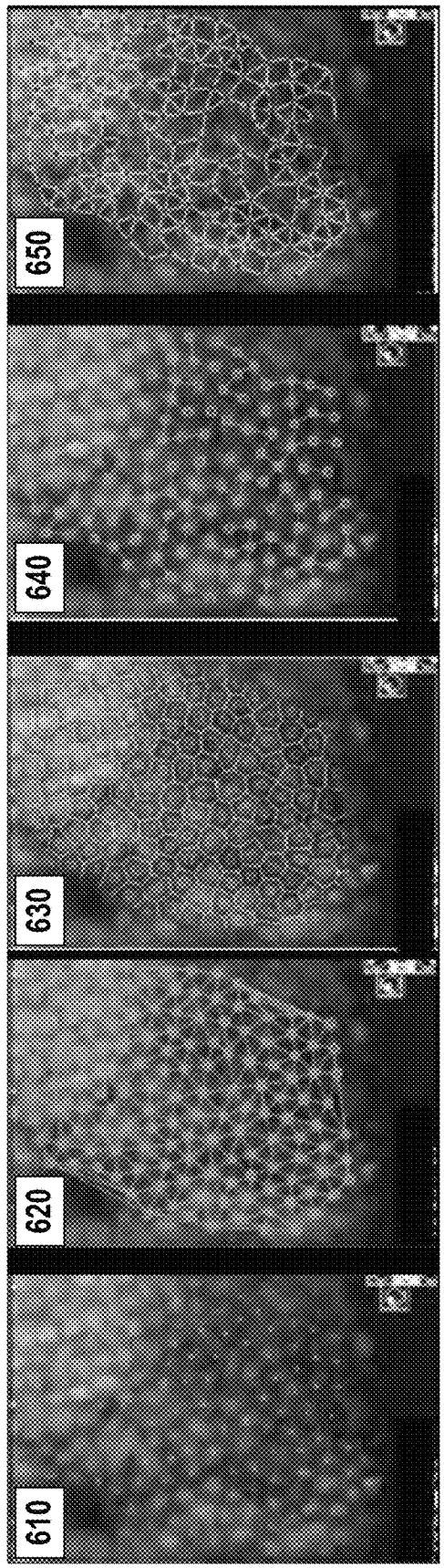
FIG. 6 illustrates example images showing four types of graph structures that can be employed to capture cell arrangement, in connection with various embodiments discussed herein.
Figure 7:
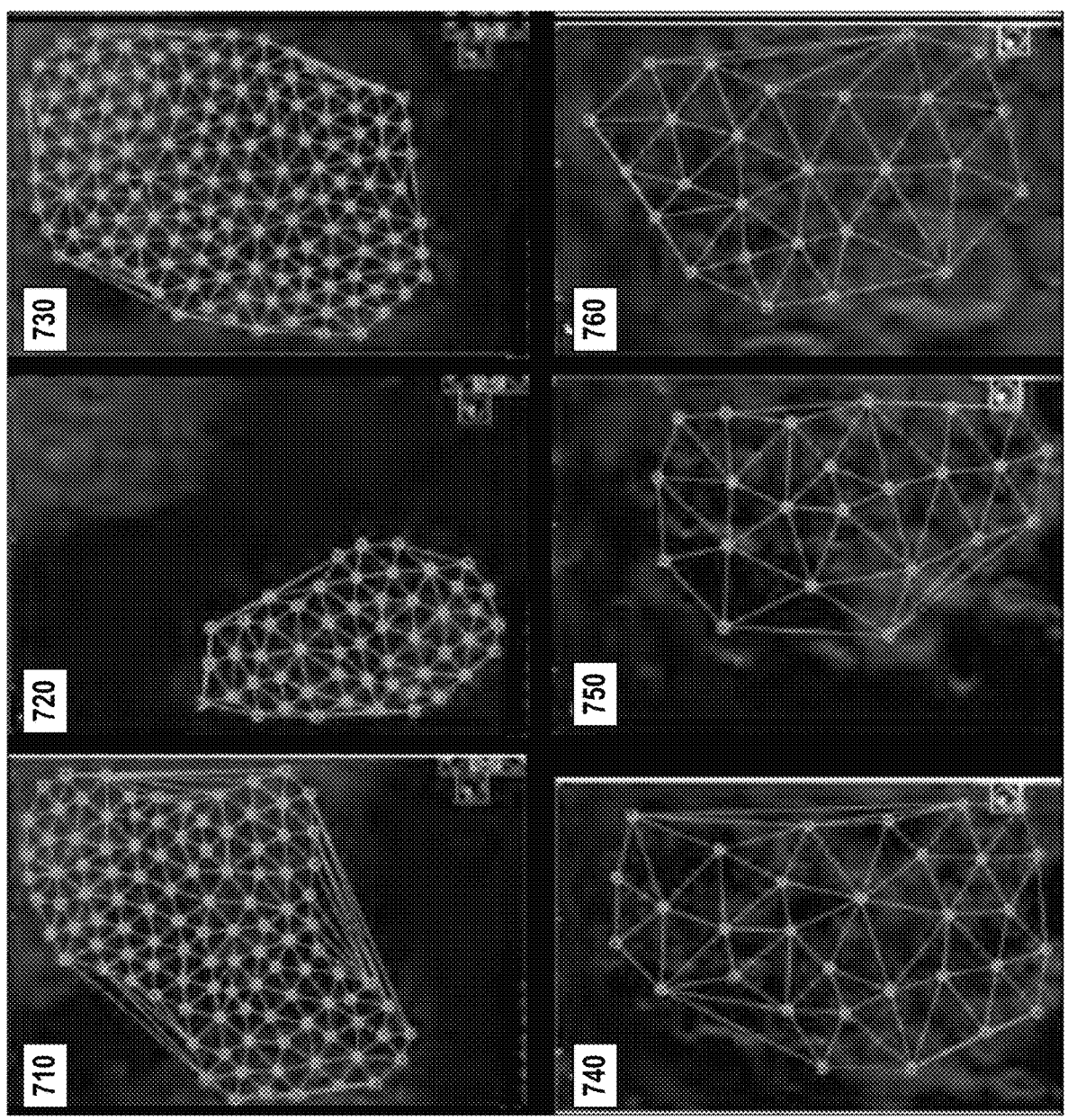
FIG. 7 illustrates example images showing Delauney graph analysis of two groups (top and bottom rows) with clear differences of centrally located, repeated EC images, in connection with various aspects discussed herein.
Figure 8:
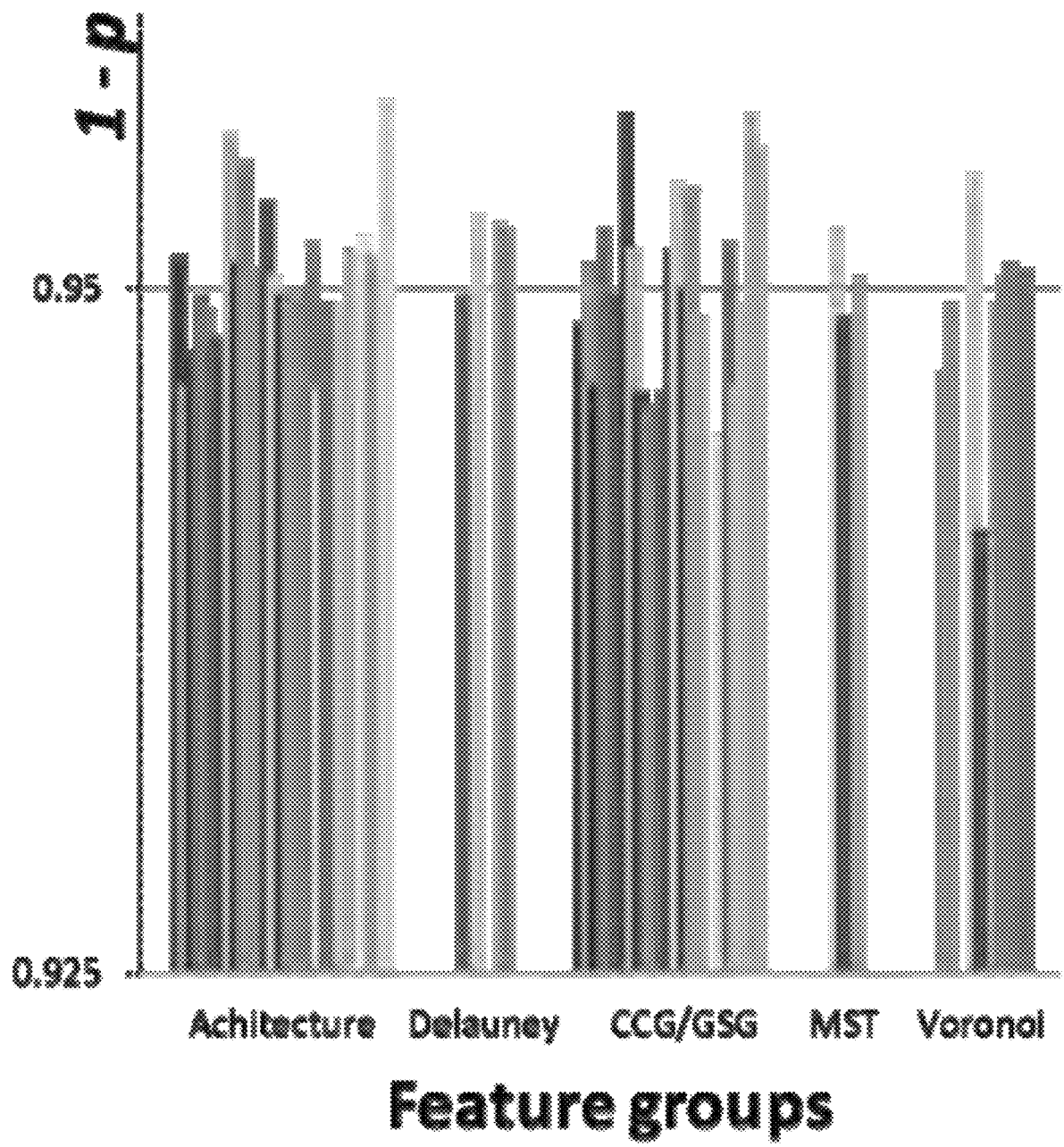
FIG. 8 illustrates a graph showing statistically different features (those above the 0.95 line) as computed from two sets of repeated, central EC images as in FIG. 7, in connection with various aspects discussed herein.
Figure 9:
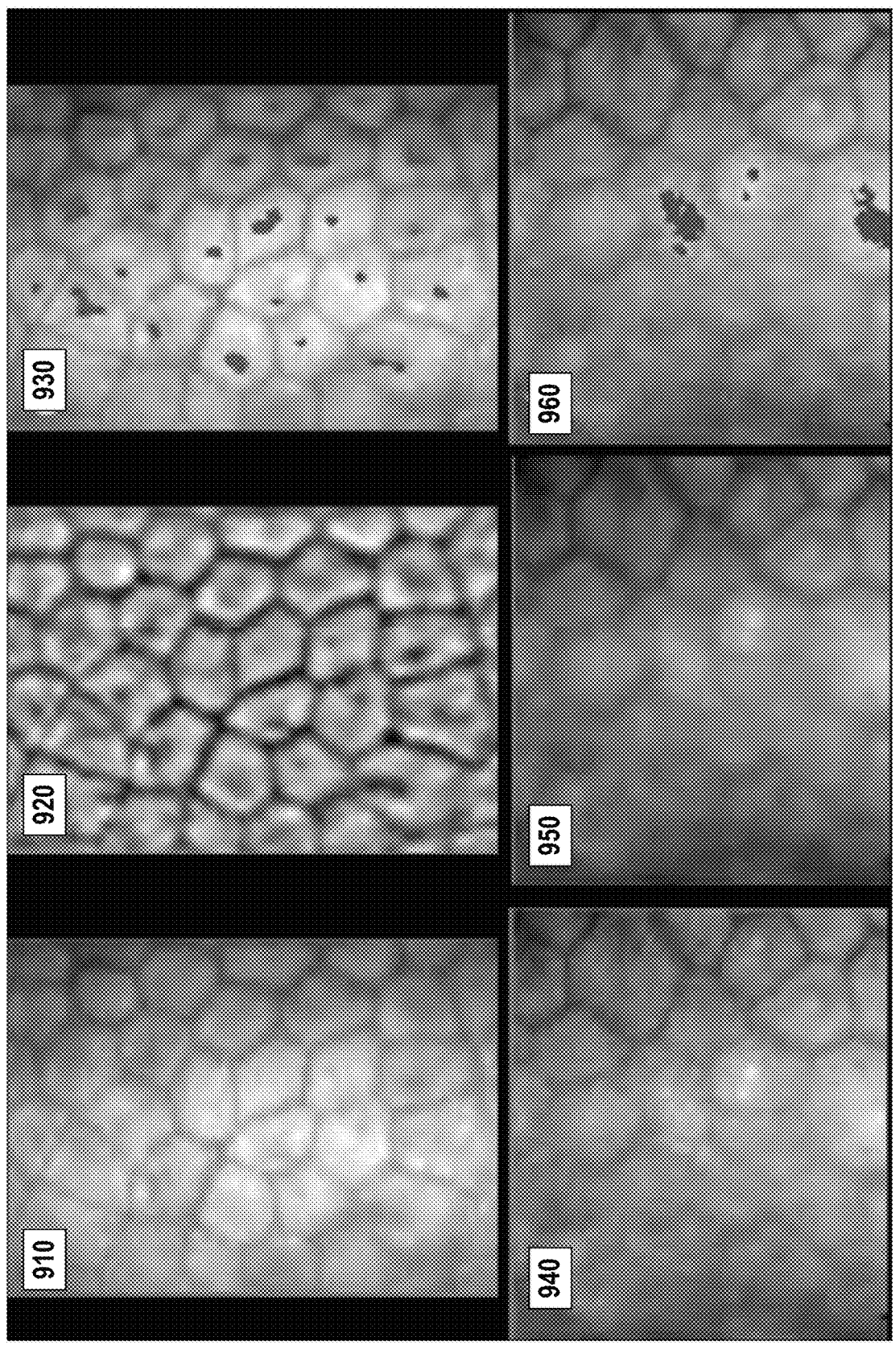
FIG. 9 illustrates images showing image processing to identify dark nuclei and bright pigments in EC images, in connection with various aspects discussed herein.
Figure 10:
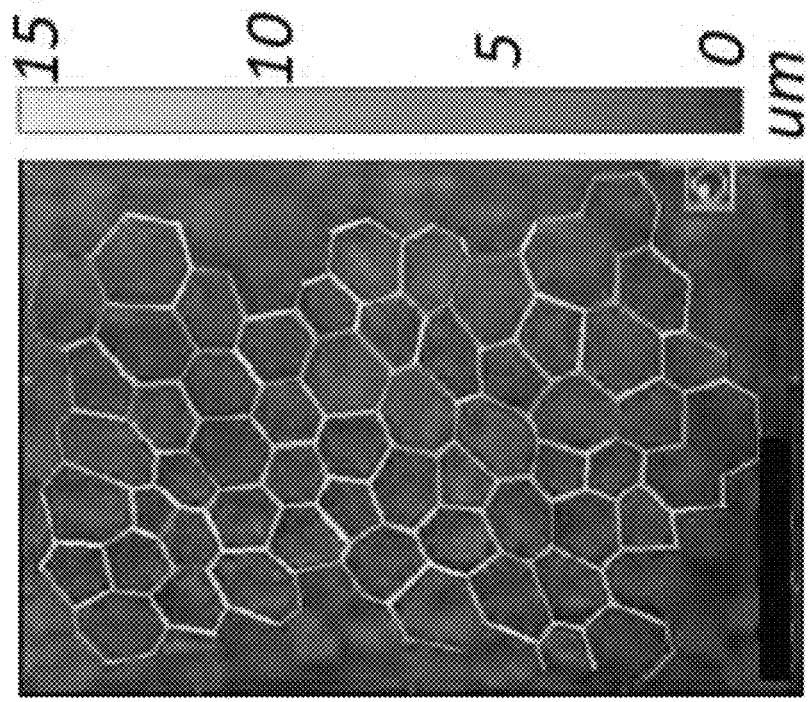
FIG. 10 illustrates a graph and heatmap of an example EC image showing variations in thickness of dark gaps between cells, measured via the full width at half-intensity-minimum of the curve (left), in connection with various aspects discussed herein.
Figure 10:
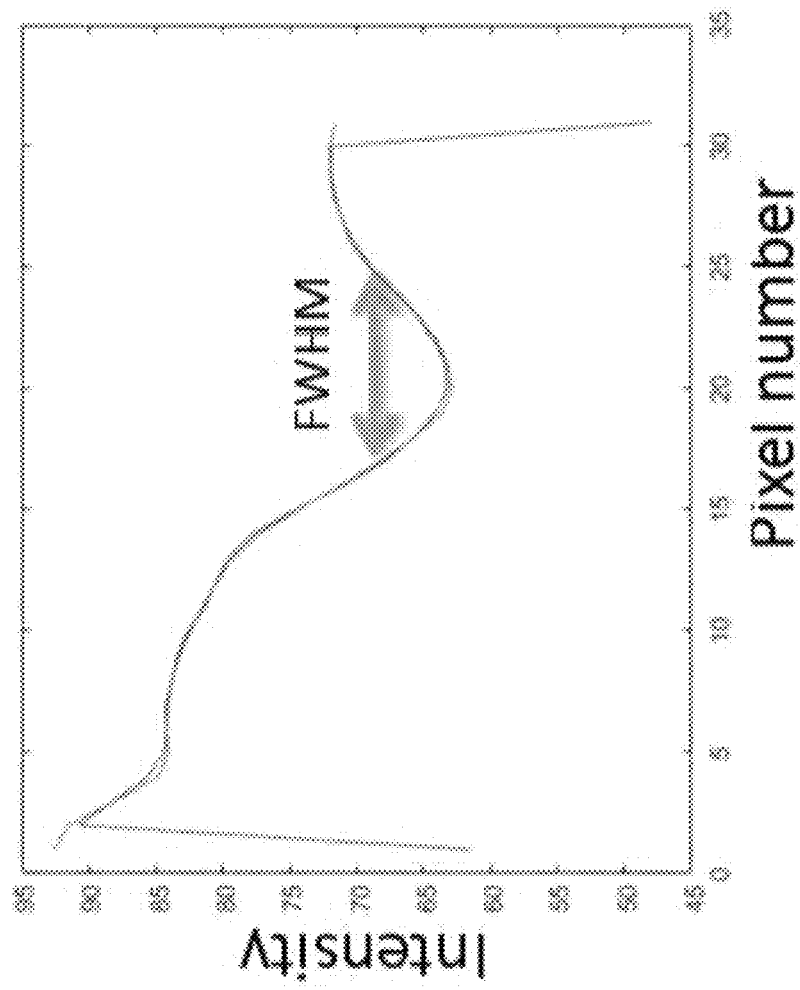
Figure 11:
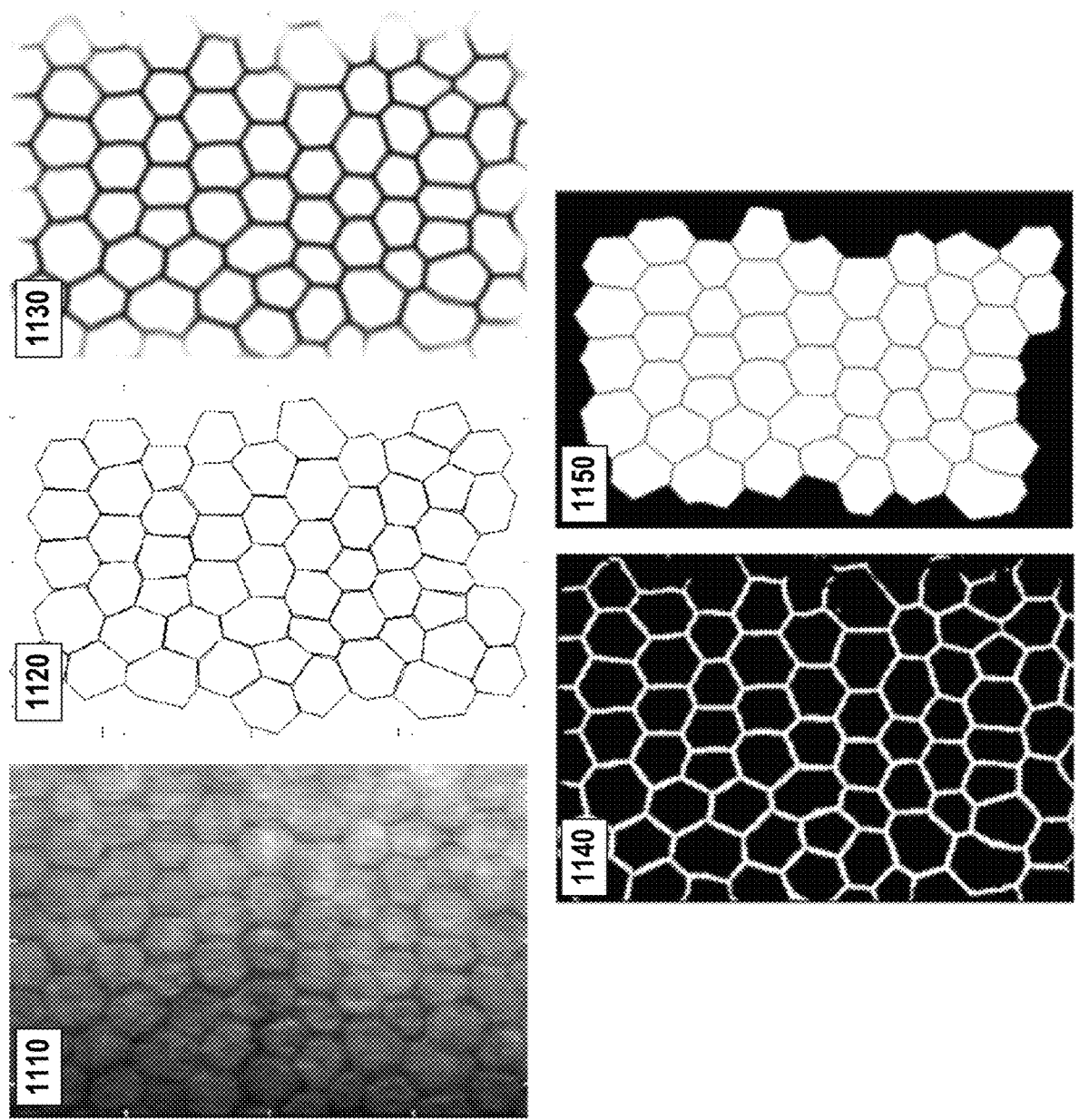
FIG. 11 illustrates example images associated with a post-processing pipeline of the example use case, in connection with various aspects discussed herein.
Figure 12:
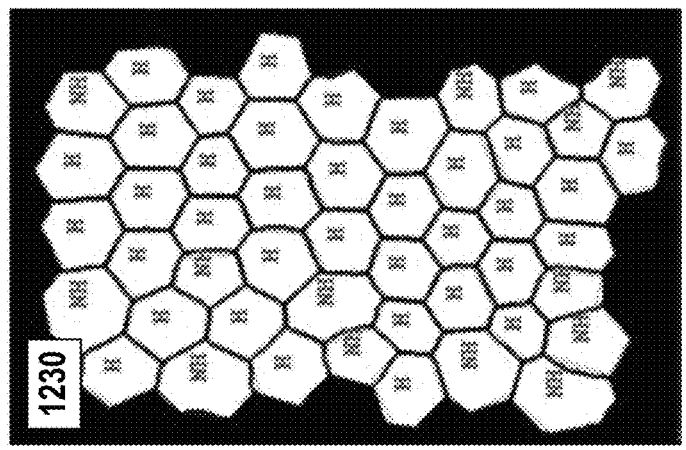
FIG. 12 illustrates example images showing hexagonality determined based on shape detector techniques of the example use case, in connection with various aspects discussed herein.
Figure 12:
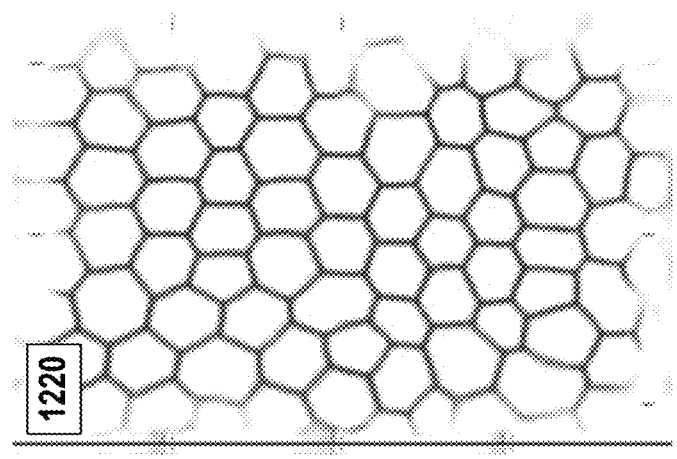
Figure 12:
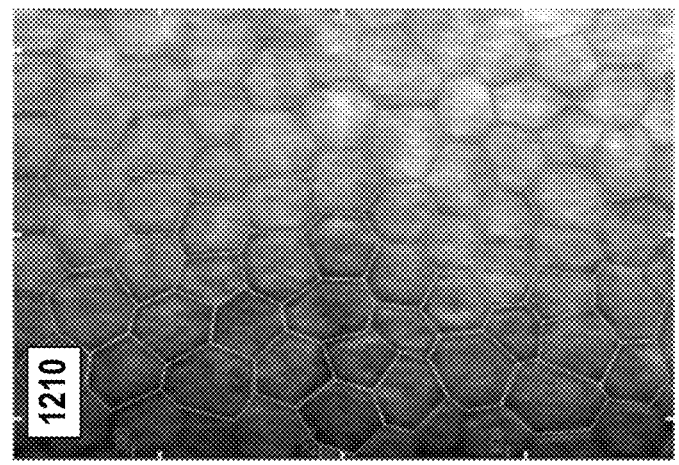
Figure 13:
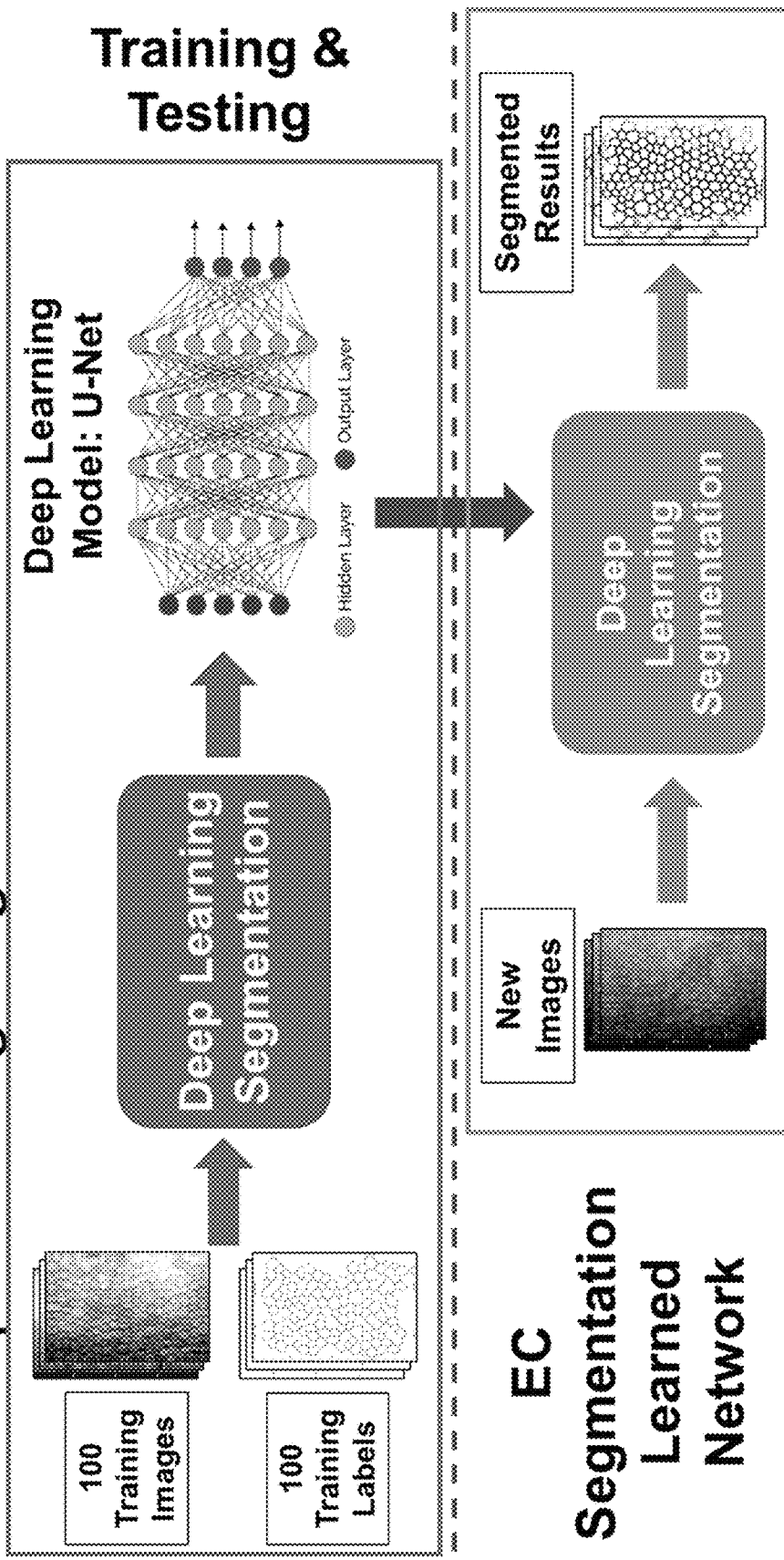
FIG. 13 illustrates a diagram showing an overview of training, testing, and application of the deep learning model for endothelial cell segmentation, in connection with various aspects discussed herein.
Figure 14:
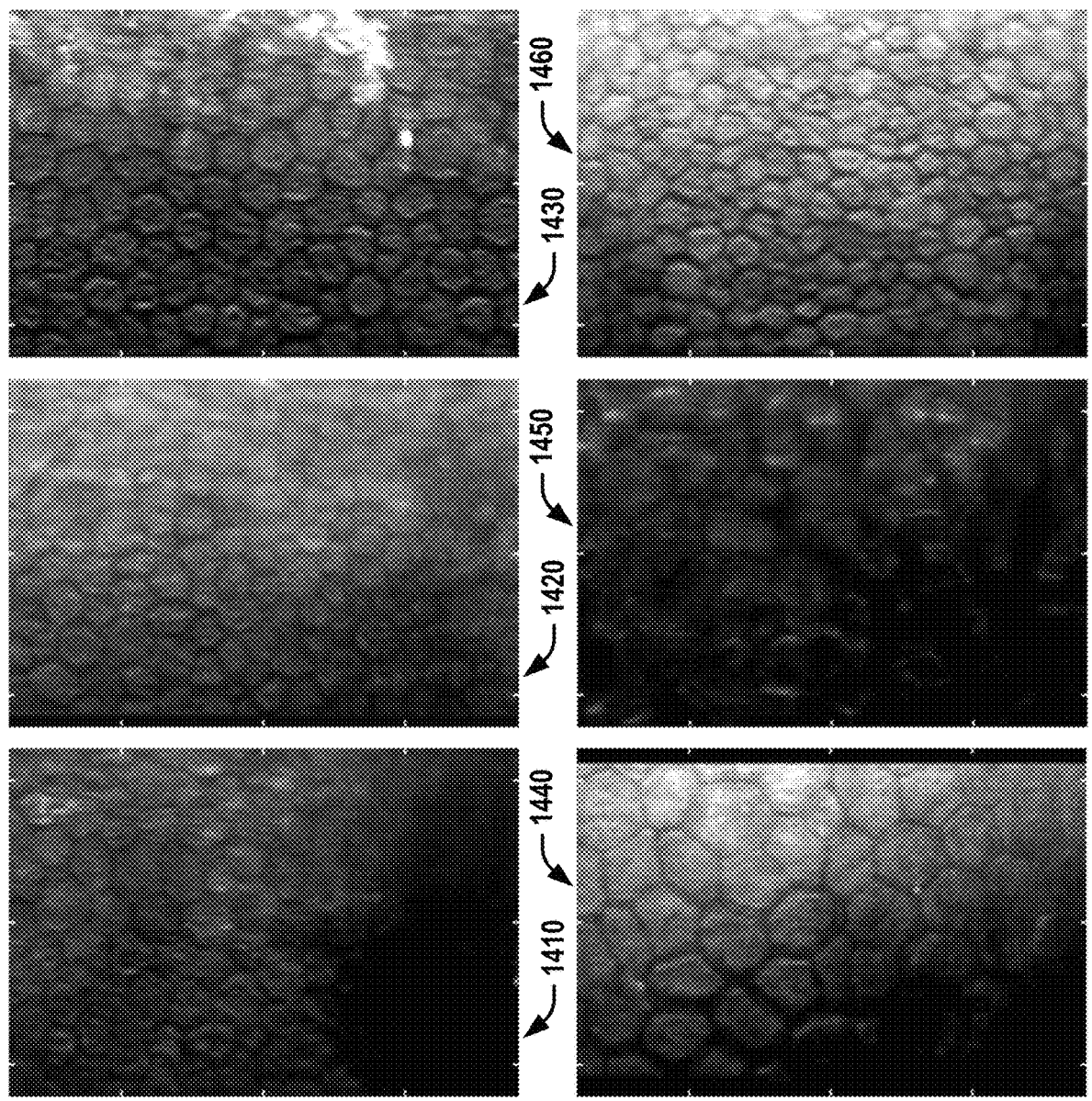
FIG. 14 illustrates specular microscopy images with varying endothelial cell density, duration post-transplant, and contrast from left to right across the image area, in connection with various aspects discussed herein.
Figure 15:
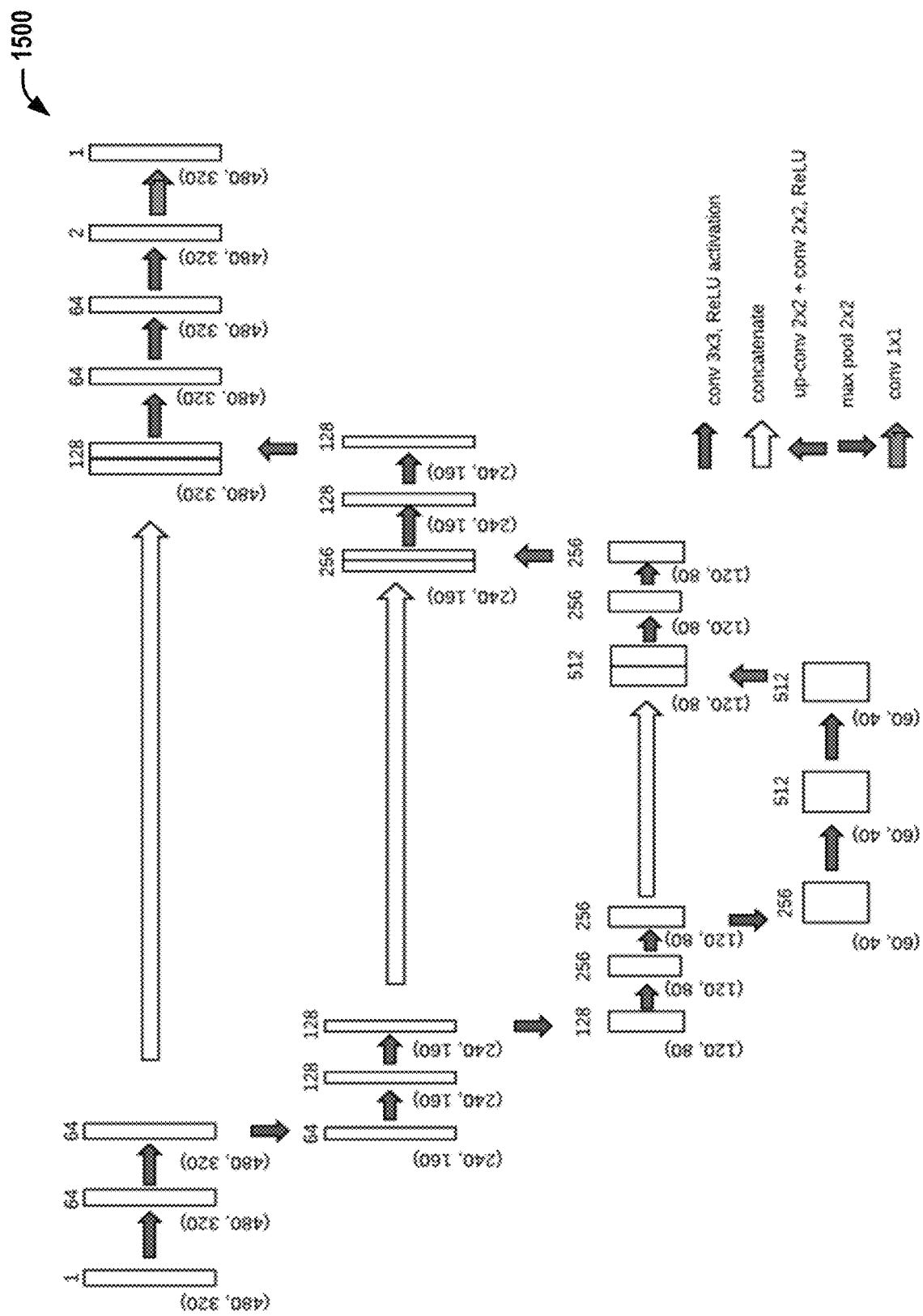
FIG. 15 illustrates a diagram showing the U-Net architecture that can be employed in connection with various aspects discussed herein.

FIGS. 5-30, discussed in greater detail below, show example images, graphs, and other information in connection with the example use case. FIGS. 5-12 relate to preliminary results during an initial stage of the example use case. FIG. 5 shows changes in EC images between 0.5-3 years as cells are lost after PK. Although the 6-month image shows good cell density, there is disarray (at 510) as compared to the very regular hexagonal structure in a normal EC layer (not shown). Among other features, the example use case used four types of graphs to capture cellular structural relationships, as shown at FIG. 6. Delaunay graphs give clear visual and quantitative differences between sets of repeated images in FIG. 7. For these same sets of images, preliminary analysis found that 32 of 80 features were statistically different (FIG. 8). Various embodiments can employ these features or other features determined to have feature stability, a highly desirable property, across repeated images. Initial analysis also noted many visual attributes of EC images that are not captured by existing quantitative biomarkers (ECD, HEX, CV). The example use case quantitatively assessed dark nuclei and bright pigments (FIG. 9) as well as thickness of dark gaps between cells (FIG. 10), using preliminary image processing algorithms. Visual assessments of such attributes have been related to keratoplasty rejection by the consultants. FIGS. 11-12 illustrate techniques for determining cell density and hexagonality (HEX). FIGS. 13-15 illustrate deep learning techniques for segmenting ECs.

Automated Segmentation of Endothelial Cells

The automated image processing pipeline to generate segmentations of endothelial cells from the example use case comprised three main steps. First, images were pre-processed to correct for shading/illumination artifacts. Second, a learning algorithm was trained to generate pixel-wise class probability maps. Finally, thresholding and morphological processing operations were performed to generate the final binary segmentation maps. Each of these steps is described in detail below.

EC images, especially specular microscopy images, are commonly associated with varying illumination across the imaging area. The example use case corrected this artifact by generating a low-pass background image using a Gaussian blur and dividing the original image with the background image. This resulted in a flattened image with even illumination across the complete field of view.

In recent years, deep learning methods (especially convolutional neural networks (CNNs)) have been extensively used to perform medical image analysis tasks, such as image classification and segmentation. CNN architectures are commonly comprised of convolutional, pooling and up-sampling layers and are trained to minimize a pre-defined loss function. Convolutional layers learn one or more filters, where the weights of the kernel filter are shared across the image. Pooling layers reduce the size of the feature maps allowing the network to be invariant to small translations. Upsampling layers allow the creation of an output probability image with the same size as the input. The U-Net network architecture was used in the example use case, but techniques discussed herein can be extended to any CNN architecture capable of performing either image segmentation or classification tasks.

U-Net was initially shown to segment neuronal structures in electron microscopy (EM) stacks with low pixel errors. Since EC images are visually similar to such stacks (both contain dark cell border regions between brighter cell regions), it was hypothesized that the network would perform well for the task of EC segmentation. The network uses skip connections to recover the full spatial resolution in its decoding layers, allowing one to train such deep fully convolutional networks for semantic segmentation. In initial experiments for the example use case, the network was trained in a ten-fold cross validation fashion over 100 images and tested on a held-out data set of 30 images. Results from the network on images from the held-out test set are shown in FIG. 19 and other figures. Dice and Jaccard coefficients obtained for U-Net using a fixed threshold and an adaptive threshold are in table 1, below.

TABLE 1

Dice and Jaccard coefficients for CNNs and thresholding techniques Cell Basis

| Metric | Minimum | Average | Maximum | Std. Dev. |
|---|---|---|---|---|
| Dice Coefficient | 0.00 | 0.87 | 0.98 | 0.17 |
| Jaccard Coefficient | 0.00 | 0.80 | 0.96 | 0.18 |

Finally, the probability maps from the neural network were binarized using one of two methods: adaptive Otsu thresholding over a neighborhood $\frac{1}{8}^{th}$ the size of the input image or a simple [7×7] sliding window local thresholding approach. In the resulting binary image, predicted cell borders are labeled white (255) and other regions labeled dark (0). A series of morphological operations are performed on the binary images to create thin strokes between cells and to clean the results. Details of the morphological operations are described in the section below.

Automated Determination of Existing EC Metrics

After obtaining segmentation results, the post-processing pipeline involves binarization, skeletonization, and morphological cleaning. Binarization was conducted via an adaptive Otsu threshold. The adaptive threshold was calculated using Otsu's threshold selection method within a sliding window approximately ⅛th the size of the segmentation resulting image. The binarized image was inversed so the end product is white cell borders with black cells and surrounding area. In other aspects, binarization can be obtained via an adaptive threshold. The adaptive threshold was calculated within a sliding window at each pixel location using the following equation: $T=m[1+k(\sigma/\sigma_{dyn}-1)]$, where T is the adaptive threshold value, m is the mean intensity in the pixel neighborhood, $\sigma$ is the standard deviation in the same neighborhood, $\sigma_{dyn}$ is the difference between the maximum and minimum standard deviation across the image, and k is a tunable parameter of the thresholding algorithm. After either technique for thresholding, the binarized image was inverted so the output comprised white cell borders with black cells and surrounding area.

Four consecutive morphological operations were employed in the example used case to create thin strokes between cells and to clean the binarized result. First, a morphological closing operation with a structuring element comprising a disk with radius 4 was performed to close cell borders with gaps from the binarization process. Second, the result was processed with a thinning operation. Thinning results in 1-pixel wide cell borders, thereby matching the width in the ground truth labels. Third, a flood-fill operation was applied, delineating all cells and borders white, and the surrounding area black. This process left small erroneous cell border segmentations outside the primary segmentation regions. A morphological area opening operation was performed that identified and removed 4-connected pixels or any connected components less than 50 pixels. Finally, this image was multiplied by the inverse of the image produced after the second manipulation. The result was a binary image with only the cell area pixels white, and all cell border and surrounding pixels colored black. An example of a raw image, its ground truth segmentation, the automated segmentation result, the binarized segmentation, and the skeletonized binary image are shown in FIG. 13.

In various embodiments, minor segmentation errors can result due to especially challenging areas within a given image or rare cell and cell border cases. To improve the automatically generated segmentations, Guided Manual Correction Software was developed in connection with the example use case, and can be used to edit the binarized segmentations. Briefly, this software allows one to view multiple images related to the automatic segmentation. The software highlights cells within the binarized segmentation that are deemed to have been segmented incorrectly by the automatic segmentation algorithm. The user then can erase or edit the cell borders utilizing built-in tools within the software. The final edited binarized segmentation will be used in subsequent processing. The algorithm for identifying potential segmentation errors is based upon deep learning probability outputs and cell areas. The Guided Manual Correction Software is discussed in greater detail in co-owned U.S. Provisional Patent Application No. 62/985,481, filed Mar. 5, 2020, and entitled "AUTOMATED SEGMENTATION AND GUIDED CORRECTION OF ENDOTHELIAL CELL IMAGES," the contents of which are herein incorporated by reference in their entirety.

To obtain the ECD from the skeletonized binary segmentation result, the total cell area was calculated by automatically counting the total number of pixels the cell area (including the cell borders) and multiplying this by the area of one pixel (0.65 um$^2$). The area of one pixel is obtained from the corresponding microscope's calibration measurements. Then a connected components tool was used to identify every cell in the region of interest; two area thresholds were used to remove the background area (>6500 um$^2$) and regions that were unrealistically small for cells (<65 um$^2$). The remaining cells were counted and noted. The ECD for each image is the number of cells divided by the total area of the cell sample region of interest.

CV calculations start with using connected components and area thresholds to identify true cells in the region of interest. Then the area of each cell was calculated individually including its border. Outliers were removed from the list of cell areas as these are the result of improper cell closings during the segmentation and post-processing steps. The standard deviation and mean of the individual cell areas are calculated, and the ratio of these two values represent the CV.

To determine the HEX value of an image, a shape detection algorithm is used to identify hexagonal versus non-hexagonal cells. The skeletonized image mentioned previously is inverted, then the white borders were dilated by 2 pixels, and finally reversed again so that the final image has white cell area with black thick borders and black surrounding area. The shape detection algorithm utilized in the example use case was based on the Ramer-Douglas-Peucker algorithm, which takes a set of points in a curve, and reduces the points to define a similar curve or line with less points, and is applied to the cell borders. Using a contour approximation, vertices were defined at the end of these curves/lines. The number of vertices per shape, or cell in this case, are counted, and if there are 6 vertices, the cell is labeled a hexagon; if there are not 6 vertices, the cell is labeled non-hexagon. HEX equals the number of hexagonal cells divided by the total number of cells in region of interest. FIG. 14 displays an example result of this shape detection algorithm.

Determination of Other Cellular Features

Hundreds of other features were computed from the segmented EC images. First, the structure of cellular arrangement was captured using graphs. Graph analytics were applied (e.g., Delaunay and cell cluster graphs, and their computed features, as shown in FIGS. 6-8). Graph analytic features comprises features for each node and/or global features. As there are a very large number of potential features, various feature selection techniques (e.g., minimum-redundancy-maximum-relevance (mRMR), etc.) were applied to identify the ones most important for determining corneas at risk. Second, cellular architectural morphometric measures were computed from single cells (e.g., area and eccentricity, etc.), in many cases using existing library computer functions. Third, a variety of hand-crafted features targeting image attributes in the literature were computed (e.g., architecture features shown in FIG. 8). These features were developed based upon image attributes related to rejection (e.g., irregular cell morphology, irregular distribution, cell nuclei, cellular reflectivity, wall thickness, etc.). Additionally, examples of new measures (wall thickness, bright pigment, and dark nucleus) are illustrated in FIGS. 9-10. For most features, statistical measures over the image (e.g., mean, standard deviation, skewness, kurtosis, and/or binned histogram, etc.) were extracted.

Determination of Corneas at Risk

Machine learning classifiers were trained on large sets of data which include EC images as well as outcomes (e.g., rejection, failure or no adverse event) and used for validation on held-out test sets. Software developed for the example use case segments ECs, extracts features as discussed above, and predicts from the EC images those cornea(s) that will experience a rejection episode or future graft failure. In addition to predicting keratoplasty outcome, various embodiments can evaluate rate of cell loss and time to event as a secondary outcome. Machine learning classifiers and classification results of various embodiments can provide highly accurate results, based on training and testing on more than 6,000 well-curated EC images obtained at multiple time points from already-collected corneal datasets, including SMAS (EY12728) applied to penetrating keratoplasty (PK) at CWRU, CPTS (EY020798) applied to Descemet stripping automated endothelial keratoplasty (DSAEK) at CWRU, and corneal EC images from the Netherlands Institute for Innovative Ocular Surgery, hereafter called CNIIOS, applied to Descemet membrane endothelial keratoplasty (DMEK).

Details. The actual classifiers can be created using support vector machine (SVM), random forest, or any number of other classification methods (e.g., a Linear Discriminant Analysis (LDA) classifier, a Quadratic Discriminant Analysis (QDA) classifier, etc.). Classifiers were built on images from multiple time-points simultaneously, 6-month post-keratoplasty images, and serial time-point images. To reduce the total number of features and improve generalizability, techniques for feature reduction were employed. Feature reduction methods (for example, minimum redundancy maximum relevance (mRMR)) were applied to reduce the number of features considered and to possibly suggest features for potential additional refinement. Another dimensionality reduction approach would be to use a Cox Proportional Hazards Model (CPHM) or the Wilcoxon rank-sum test to determine features most indicative of a future adverse event (rejection or failure). Performance was assessed using cross-validation experiments and the number of trials was increased by rotating fold membership. Classifiers can be tuned appropriately. Since the number of no-adverse events greatly exceeds the number of rejection episodes and graft failures in the datasets, steps can be taken for training with imbalanced data. Feature stability was assessed across the 3 image repeats using intra-class correlation coefficient and optionally a latent instability score championed by others. If deemed appropriate, a second feature stability test was run comparing good and fair quality images routinely labeled by CIARC. In other embodiments, deep learning techniques can be employed in place of machine learning classifiers to distinguish EC images between no-adverse event vs. failure and/or no-adverse event vs. non-rejection failure vs. rejection.

Additional work in connection with the example use case comprises collecting over 900 images from the NIIOS dataset. Based on these images, automatic and guided cell segmentation can be conducted. Based on the segmented images, features can be calculated, which can comprise standard features, graphical features, and/or novel features. From the calculated features, classification experiments can be performed on the EC features to determine the ability to classify keratoplasties prone to rejection.

FIGS. 5-27, discussed below, show example images, graphs, and other information in connection with the example use case.

Referring to FIG. 5, illustrated are serial specular microscope imaging following a PK procedure, in connection with various aspects discussed herein. Images 510-540 were taken at 6 months, 1 year, 2 years, and 3 years, respectively, and show a continuing decrease (2684, 2027, 1430, 1184 cells/mm$^2$, respectively) in cell density. This eye later became dysfunctional. Notably, although there is a high density of cells at 6 months, there is variation in cell size and irregular non-hexagonal arrangement, showing disarray as compared to the very regular hexagonal structure in a normal EC layer. Various embodiments can predict eyes at risk from such images using machine learning.

Referring to FIG. 6, illustrated are example images showing four types of graph structures that can be employed to capture cell arrangement, in connection with various embodiments discussed herein. Cell centers were marked in the EC image 610. In 620-650, the graphs shown are Delauney, Voronoi, minimum spanning tree (MST), and cell cluster graph (CCG), respectively. Many computational features were computed from the graphs, for example, average area from Voronoi, average eccentricity from cell cluster graph, standard deviation of edge length from MST, etc.

Referring to FIG. 7, illustrated are example images showing graph analysis of two groups (top and bottom rows) of centrally located, repeated EC images, in connection with various aspects discussed herein. Delauney graphs show clear visual differences between the two groups. Features from the graphs showing statistically significant differences ($p<0.05$, as shown in FIG. 8) included standard deviation of triangle area from Delauney, average chord length from Voronoi, disorder of edge length from MST, and percentage of isolated points from CCG.

Referring to FIG. 8, illustrated is a graph showing statistically difference features (those above the 0.95 line) as computed from two sets of repeated, central EC images as in FIG. 7, in connection with various aspects discussed herein. Features shown in FIG. 8 were computed from 4 graph types (as in FIG. 6) and from tissue architecture (e.g., average distance to 7 nearest neighbors, although a different number of neighbors can be used in various embodiments). A permutation test was used to evaluate significance. Of the 80 features in the categories of FIG. 8 that were evaluated, 32 were significantly different ($p<0.05$) and more were nearly significant. FIG. 8 shows examples of features that can be created that show differences between groups of EC images. One criterion for good features is stability across repeated images, and additional, less preliminary results are discussed below. Various embodiments can employ any of a variety of features discussed herein for classification of EC images (e.g., as normal vs. failure risk, or normal vs. non-rejection failure risk vs. rejection risk, etc.).

The example use case identified many visual attributes of EC images that are not captured by existing quantitative biomarkers (ECD, HEX, CV). Referring to FIG. 9, illustrated are images showing image processing to identify dark nuclei (910-930) and bright pigments (940-960) in EC images, in connection with various aspects discussed herein. For dark nuclei, starting with segmented cells, intensity background variation was corrected and noise reduced (920, 950), and conditional dilation was applied to a threshold. Small regions were removed. Bright pigments (940-960) were processed similarly. Referring to FIG. 10, illustrated are a graph and heatmap of an example EC image showing variations in thickness of dark gaps between cells, in connection with various aspects discussed herein. On the right of FIG. 10 is shown a heatmap of "dark gaps" between cells. Starting with segmented cells, the full width of the half-intensity-minimum of the curve was measured, as shown on the left of FIG. 10. The curve is an average of 11 perpendicular lines extracted from the midway point of a side. Gaps can be accentuated by lateral distances as well as potentially cell height in these obliquely illuminated images. Visual assessments of attributes such as those shown in FIGS. 9-10 have been related to keratoplasty rejection by the consultants.

FIGS. 11-12 show techniques related to determining endothelial cell density (ECD) and hexagonality (HEX). Referring to FIG. 11, illustrated are example images associated with a post-processing pipeline of the example use case, in connection with various aspects discussed herein. FIG. 11 shows the following in connection with a post-processing pipeline for an example image: (a) Corneal endothelium image captured via specular microscopy at 1110; (b) ground truth segmentation at 1120; (c) U-Net segmentation probability result at 1130; (d) binarized segmentation at 1140; and (e) skeletonized segmentation at 1150. Referring to FIG. 12, illustrated are example images showing hexagonality determined based on techniques of the example use case, in connection with various aspects discussed herein. FIG. 12 shows the following results: (a) Corneal endothelium image and corner analysis with borders in green at 1210; (b) probabilities from the deep neural network at 1220; (c) results of algorithm on binarized network outputs with H=hex and NH=non-hex at 1230.

Referring to FIG. 13, illustrated is a diagram showing an overview of training, testing, and application of the deep learning model for endothelial cell segmentation, in connection with various aspects discussed herein. The deep learning segmentation algorithm in the example use case started with 100 EC images and corresponding manual annotation labels to train a deep learning network called U-Net. U-Net can learn features from the training images and labels so it can classify a pixel as either cell border, or cell and surrounding area. Once trained, additional EC images (e.g., from a test set, patient imaging, etc.) can be provided to the EC segmentation learned network to generate segmented results. For the example use case, of 130 EC images, 30 were in the held out test set, and the remaining 100 were used with 5-fold cross validation to train the model for subsequent testing on the 30 held out test images.

Referring to FIG. 14, illustrated are example specular microscopy images 1410-1460 with varying endothelial cell density, duration post-transplant, and contrast from left to right across the image area, in connection with various aspects discussed herein.

Referring to FIG. 15, illustrated is a diagram showing an example U-Net architecture that can be employed in connection with various aspects discussed herein. In FIG. 15, the numbers on top and the left bottom corner of each tensor indicate the number of channels/filters and its height and width respectively. The network comprises multiple encoding and decoding steps with three skip connections between the layers (white arrows). The remaining arrows are as follows: the blue rightward arrow is a convolution with (3, 3) filter size, ReLU activation; the upward arrow is an up-convolution with a (2, 2) kernel using max pooling indices from the encoding layers; the downward arrow is a max pooling with a (2, 2) kernel; and the pink rightward arrow with a "1" in the arrowhead is a (1, 1) convolution with sigmoid activation.

Figure 16:
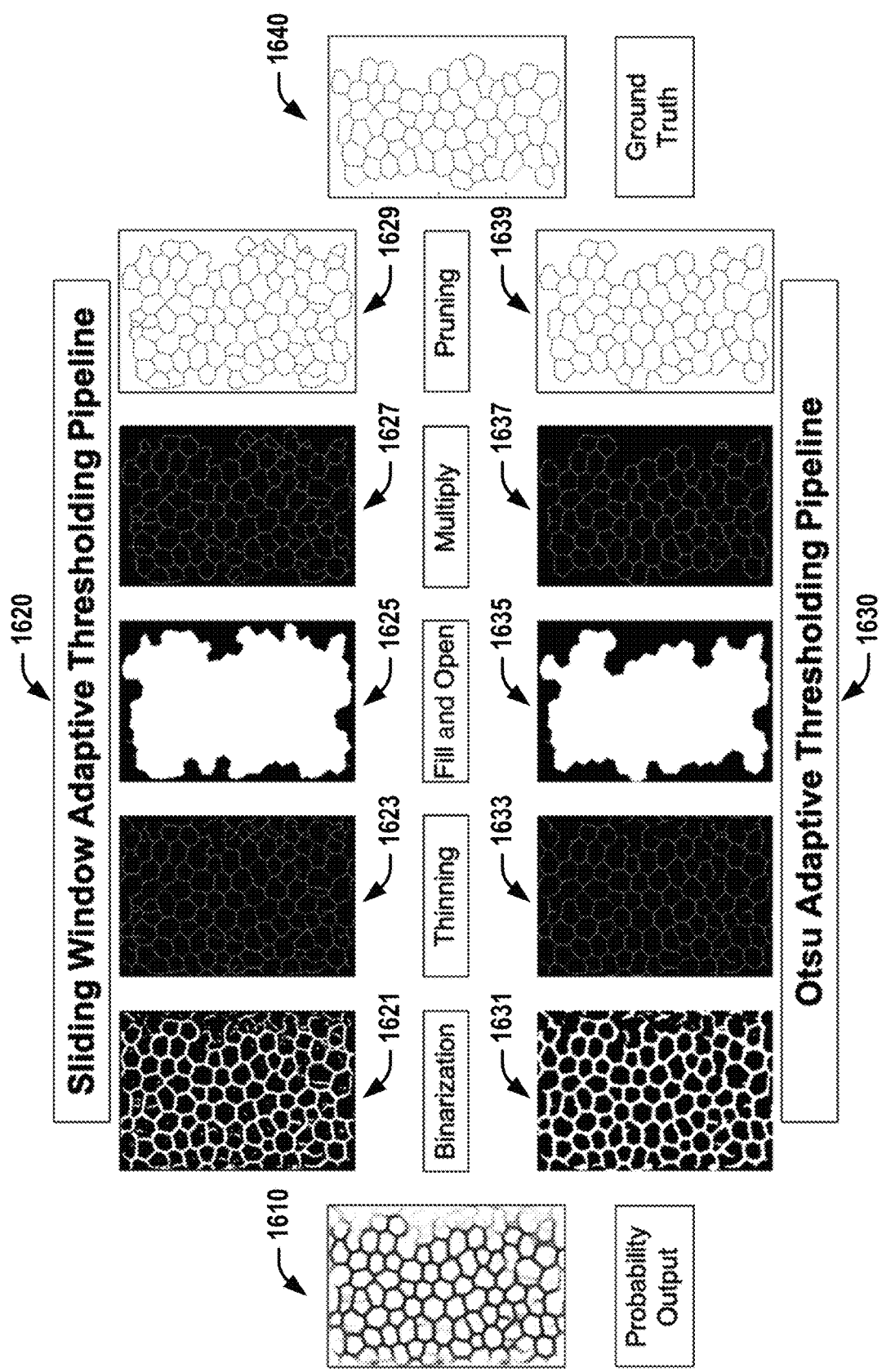
FIG. 16 illustrates images showing two different thresholding techniques that can be employed to convert probability outputs to binarized outputs, followed by a post-processing pipeline consisting of four morphological operations, in connection with various embodiments.

Referring to FIG. 16, illustrated are images showing two different thresholding techniques that can be employed to convert probability outputs to binarized outputs, in connection with various embodiments. Sliding window adaptive thresholding (1620, comprising 1621-1629) and adaptive Otsu thresholding (1630, comprising 1631-1639) were used to convert probability outputs from the U-Net algorithm (e.g., example probability output image 1610) to binarized, single-pixel width cell borders (e.g., examples 1629 and 1639) which can be compared to ground truth labels (e.g., example ground truth labeling 1640). For adaptive threshold, the steps are: binarization (1621), thinning to obtain single pixel wide lines (1623), filling and opening to remove extraneous branches (1625), multiplication with 1623 to obtain the cells borders that fully enclose cells (1627), and finally pruning to remove small spurious segments (1629). Image 1629 was compared to the ground truth label image 1640 for training and testing. Adaptive Otsu (1630) was processed the same way, at 1631-1639.

Figure 17:
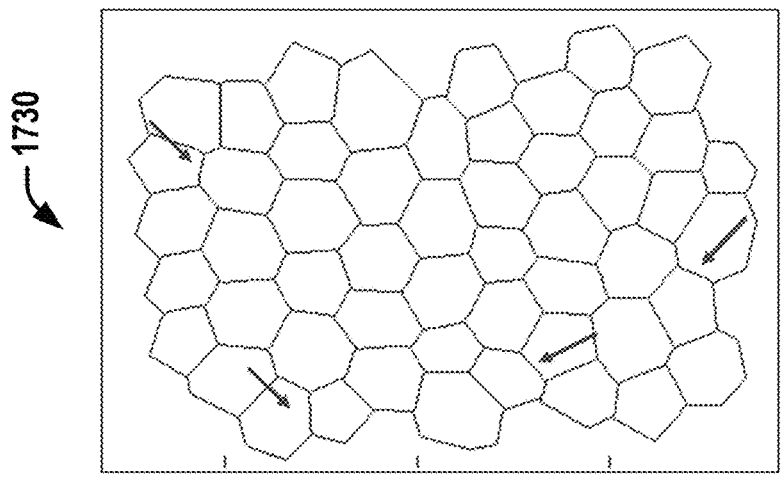
FIG. 17 illustrates images showing an example endothelial cell image, manual cell segmentation analysis, and the corresponding ground truth, corrected for border overlaps, used in the example use case, in connection with various aspects discussed herein.
Figure 17:
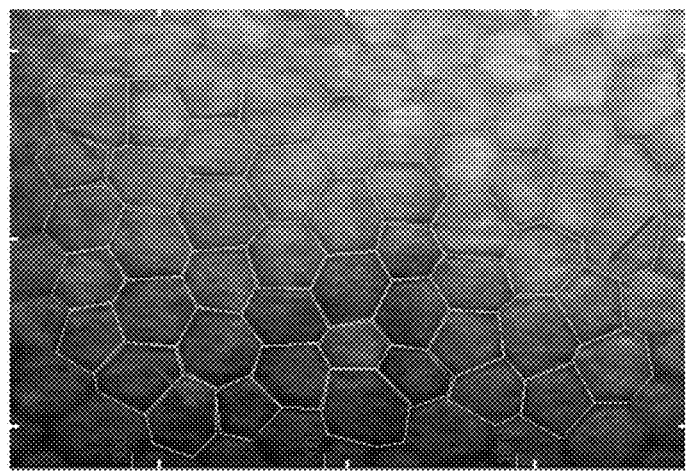
Figure 17:
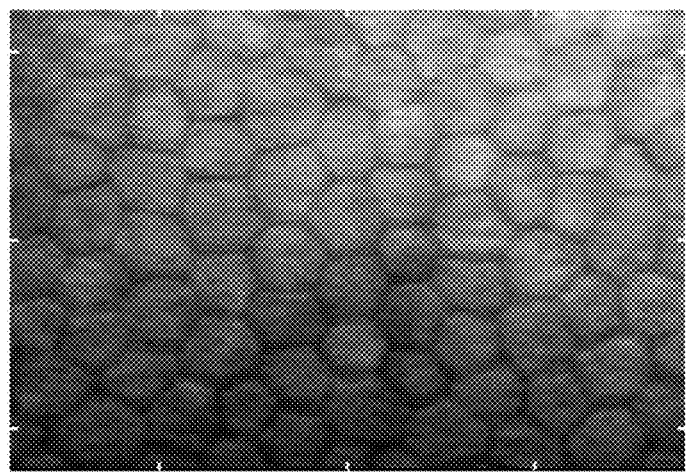

Referring to FIG. 17, illustrated are images showing an example endothelial cell image, manual cell segmentation analysis, and the corresponding ground truth, corrected for border overlaps, used in the example use case, in connection with various aspects discussed herein. At 1710 is a good quality sample EC image with cells of various shapes and sizes, showing the consistently-obtained brightness variation from left to right. At 1720 is the cell-border segmentation overlay created by an analyst using the HAI CAS software. In this good quality image, segmentations were obtained throughout the image (cells cut-off at the boundaries of the image are not labeled). At 1730 is the binary segmentation map used as a ground-truth label image. The arrows indicate example double borders generated by the HAI-CAS software in 1720 that were replaced with single borders in 1730 following processing).

Figure 18:
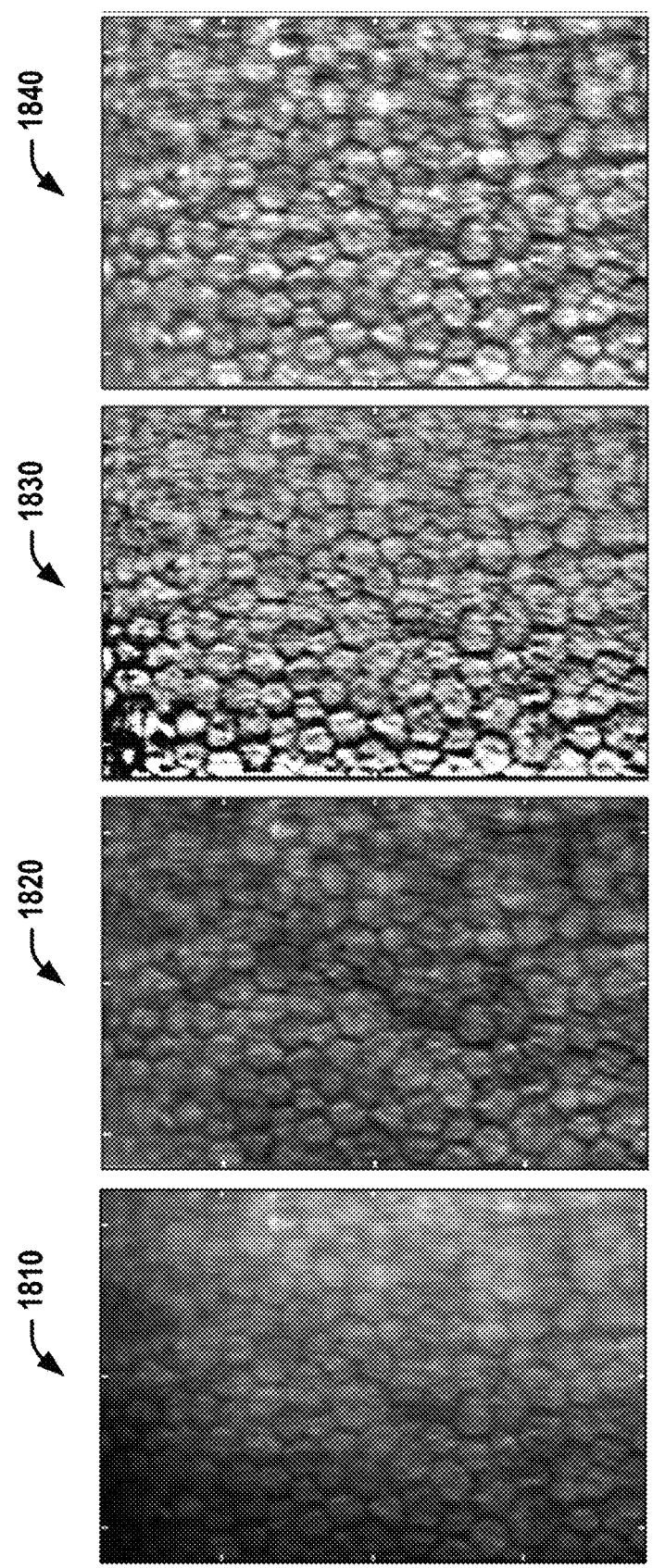
FIG. 18 illustrates example images showing three pre-processing shading correction methods applied to a representative EC image, in connection with various aspects discussed herein.

Referring to FIG. 18, illustrated are example images showing preprocessing shading correction methods applied to a representative EC image, in connection with various aspects discussed herein. The original image 1810 is corrected via localization (1820), division (1830), and subtraction (1840) methods. Each of the correction methods significantly flattened the image. For the division method, a low-pass background image was generated using a Gaussian blur and divided the original image by the background image to create a flattened image. A normalized Gaussian filter with standard deviation $\sigma=21$ pixels and a kernel foot print (65×65 pixels) was used, the 99th percentile of the flattened unit 8 image's intensity was set to the maximum intensity (255), and then the rest of the image's intensity was normalized so its distribution expanded the (0 to 255) intensity range. For the subtraction method, a low-pass background image was generated via the same Gaussian blur previously mentioned, and then this background image was subtracted from the original image, wherein the flattened image was normalized using the same method as before. For the localization method, the brightness was normalized along the vertical and horizontal directions by adding the difference between the average image brightness and the average brightness in the corresponding row/column at each pixel. New pixel values were given as $$p'(x, y) = p(x, y) + \left[L - \sum_j \frac{p(x, j)}{H}\right] + \left[L - \sum_i \frac{p(i, y)}{W}\right],$$

where p'(x, y) is the new pixel value, p(x, y) is the original pixel value, L is the average brightness in the image, H is the height of the image, and W is the width of the image.

Referring to FIG. 19A, illustrated are images of deep learning probability maps of an example test image following four types of preprocessing, in connection with various aspects discussed herein. An original test image 1900 was processed with deep learning following no preprocessing 1902, localization preprocessing 1904, division preprocessing 1906, and subtraction preprocessing 1908. In the center of the probability outputs, the borders appear more black due to the high confidence of the trained algorithm in these regions, however, toward the edges and some blurry areas of the original images, the borders appear more gray because the algorithm is less confident here (indicated by arrows).

Referring to FIG. 19B, illustrated are images showing the final segmentation results of the EC image of FIG. 18 with the four preprocessing methods discussed above, according to various aspects discussed herein. At 1950 is the ground truth label. The final segmentation results shown in 1952-1958 are: after no preprocessing (1952), after localization preprocessing (1954), after division preprocessing (1956), and after subtraction preprocessing (1958). The dashed circles indicate correct cell segmentation, whereas the solid circles indicate incorrect cell segmentation. The arrows indicate regions of newly segmented cells not previously annotated.

Referring to FIG. 20A, illustrated are three example EC images (2000, 2004, and 2008) and corresponding segmentation (2002, 2006, and 2010) highlighting cells with differences between manual and automatic segmentations, in connection with various aspects discussed herein. Cell boundaries solely identified via manual segmentation are in green, those identified via both are in yellow, and boundaries solely identified via automatic segmentation are in red. Images 2000 and 2002 shows two examples in white circles where the automated method first split a single cell and then merged two cells into one cell. The reviewers agreed the manual annotations were more accurate than the automated segmentations. Images 2004 and 2006 illustrates an example where the automated method merged two cells into one cell, and the reviewers concluded the case equivocal because it was unclear which method actually segmented the cell correctly. Images 2008 and 2010 shows an example where the automated method split one of the manually annotated cells into two cells. The reviewers considered this case to have been segmented more accurately by the automated method than the manual annotation.

Referring to FIG. 20B, illustrated are three examples of EC images showing the automatic segmentation method identifying and segmenting cells outside of the sample area of the ground truth annotations, in connection with various aspects discussed herein. Images 2050, 2054, and 2058 are sample EC image from the independent held-out test set, and images 2052, 2056, and 2060 show the respective ground truth (green) and automatic (red) segmentations overlaid, showing cells outside of the ground truth sample area segmented by the U-Net algorithm.

Figure 21:
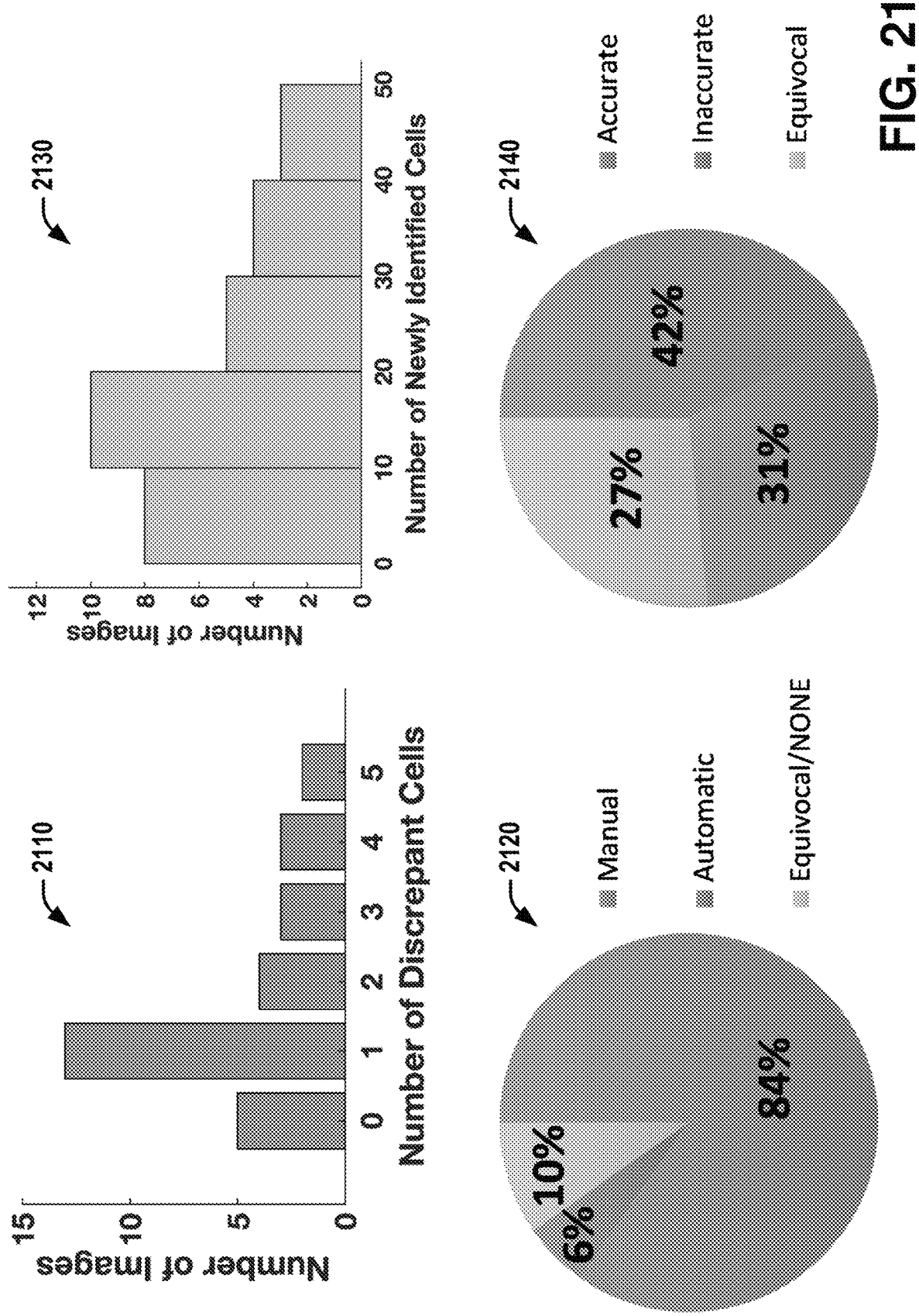
FIG. 21 illustrates charts showing the results of visual analysis of automated cells in a held-out test set comprising 30 images, in connection with various aspects discussed herein.

Referring to FIG. 21, illustrated are charts showing the results of visual analysis of automated cells in a held-out test set comprising 30 images, in connection with various aspects discussed herein. Within the manually analyzed regions, experts identified that only 52 of 1876 cells (3%) required reconsideration. A histogram of numbers of discrepancies are shown at 2110, where 22 images (73%) contained 0, 1, or 2 potential discrepancies. Notably, among discrepancies, the automated result was deemed better or equivocal 16% of the time, giving only 44 (2.3%) of cells where experts deemed it desirable to change the automated result, as seen at 2120. In the regions newly segmented by the automated method, 564 new cells (an increase of 30%) were identified, with the image histogram shown at 2130. Nearly 70% or 390 of newly segmented cells were deemed acceptable (accurate or equivocal in the pie chart at 2140).

Figure 22:
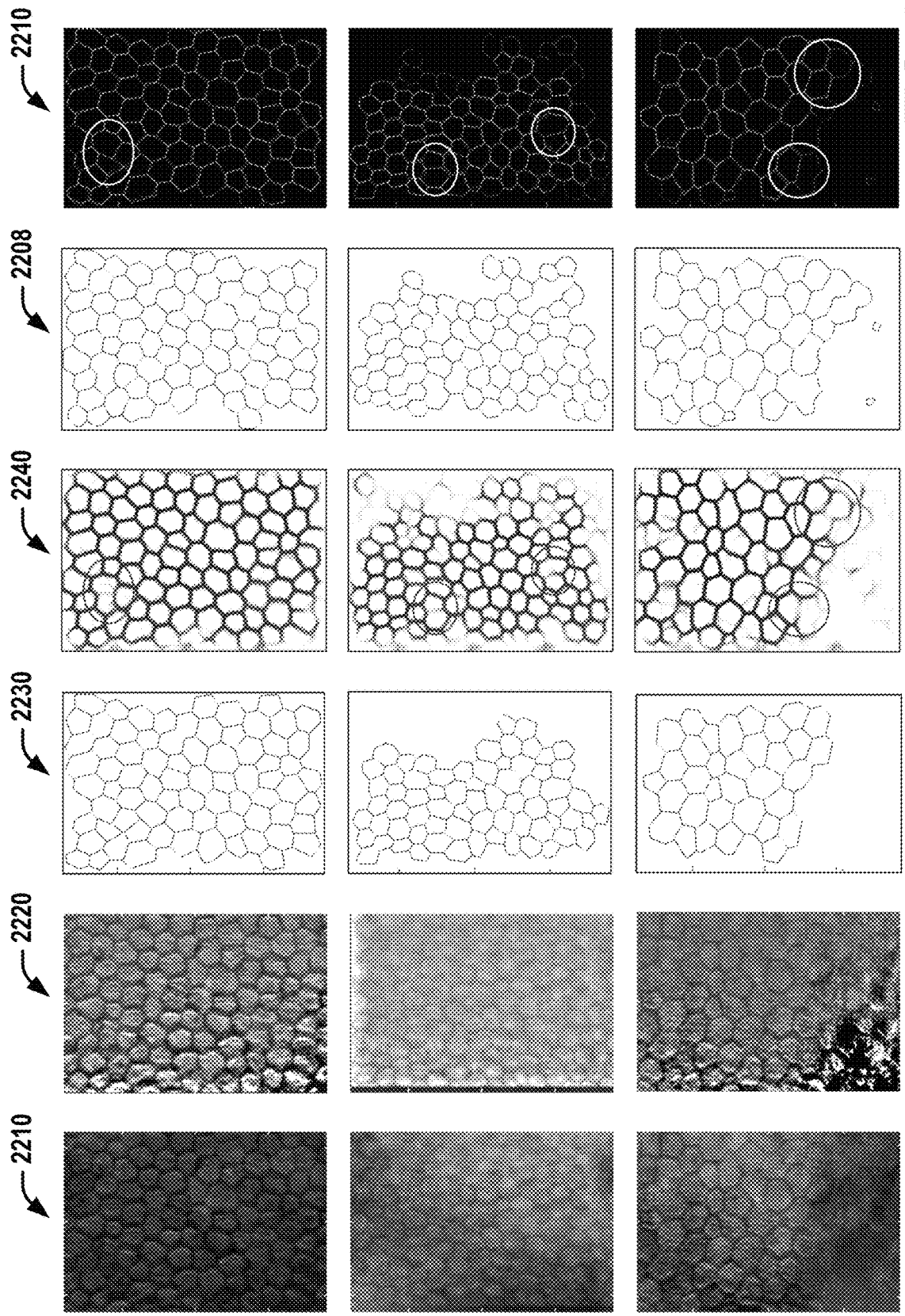
FIG. 22 illustrates images showing three example post-DSAEK EC images (corresponding to the three rows) having undergone both manual and automatic segmentation, in connection with various aspects discussed herein.

Referring to FIG. 22, illustrated are images showing three example post-DSAEK EC images (corresponding to the three rows) having undergone both manual and automatic segmentation, in connection with various aspects discussed herein. Column 2210 shows the original, raw EC images. Column 2220 shows the enhanced, pre-processed EC images. Column 2230 shows the ground truth images corrected. Column 2240 shows the U-Net probability outputs. Column 2250 shows the final border segmentations following post-processing pipeline. Column 2260 shows an overlay of ground truth manual segmentations (green) and automatic segmentations (red). Yellow indicates where the manual and automatic segmentations overlapped.

Figure 23:
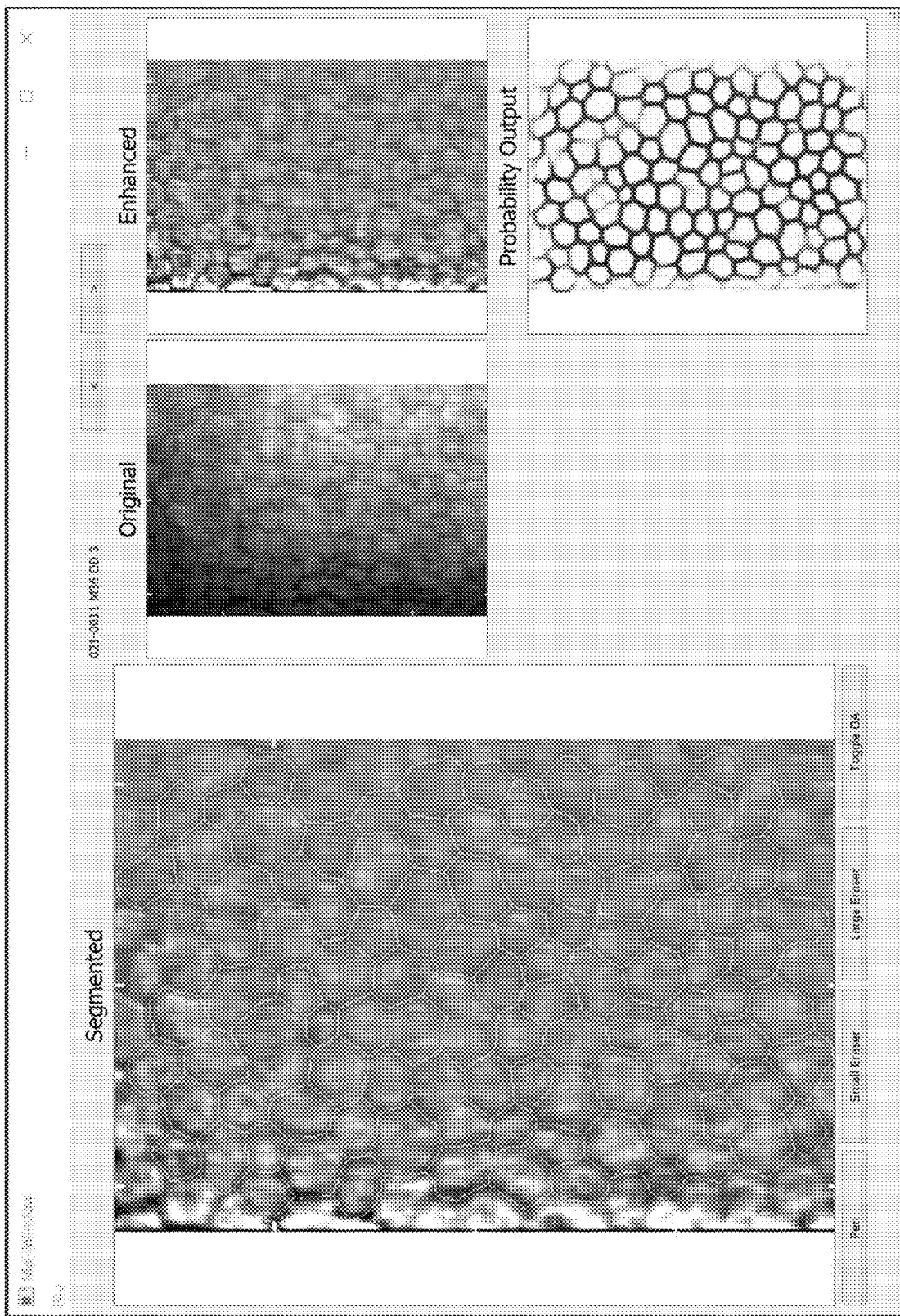
FIG. 23 illustrates an example screenshot of semi-automated segmentation graphic user interface (GUI) software, in connection with various aspects discussed herein.

Referring to FIG. 23, illustrated is an example screenshot of semi-automated segmentation graphic user interface (GUI) software, in connection with various aspects discussed herein. In the large viewing window, the GUI displays the enhanced EC image with the automatic segmentations overlay. On the side, the user can see the original raw EC image, the flattened, enhanced EC image, and the probability output to cross reference information and to aid during the manual editing process. Below the large viewing window, the user has the option to select a pen for adding cell borders, and two sizes for erasing cell borders. There is also a button to toggle between the automatic border segmentation and the highlighting of cells that may require a second review.

Figure 24:
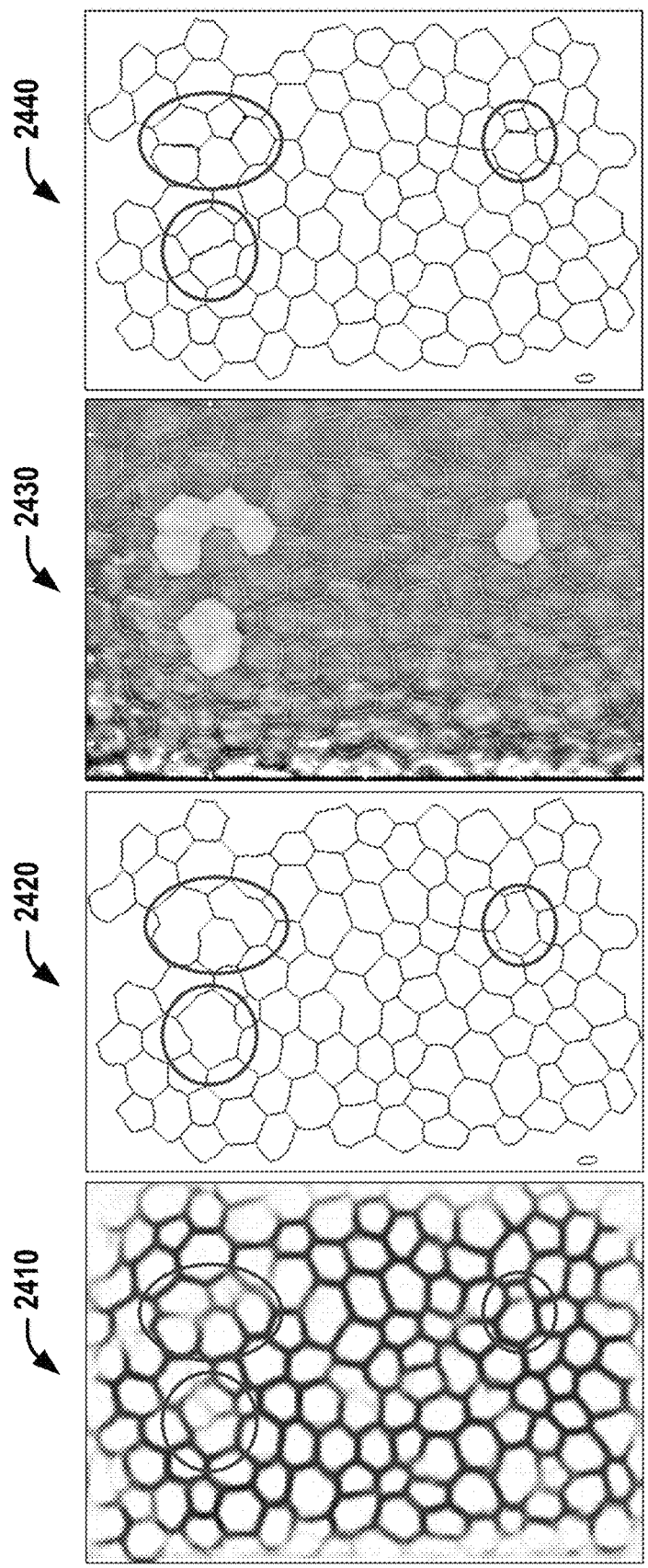
FIG. 24 illustrates example images showing cells with outlier areas or cells that were under-segmented and/or had faint or incomplete borders noticeable in the corresponding cell's area of the probability output, in connection with various aspects discussed herein.

Referring to FIG. 24, illustrated are example images showing cells with outlier areas or cells that were under-segmented and/or had faint or incomplete borders noticeable in the corresponding cell's area of the probability output, in connection with various aspects discussed herein. Circles indicate cells that matched these two conditions. At 2410 is the U-Net probability output. At 2420 is the final automatic segmentations. At 2430 is the enhanced EC imaged with automatic segmentation overlay and erroneous cells highlighted for second review. At 2440 are manual edits applied to automatic segmentation using the pen tool in the GUI software.

Figure 25:
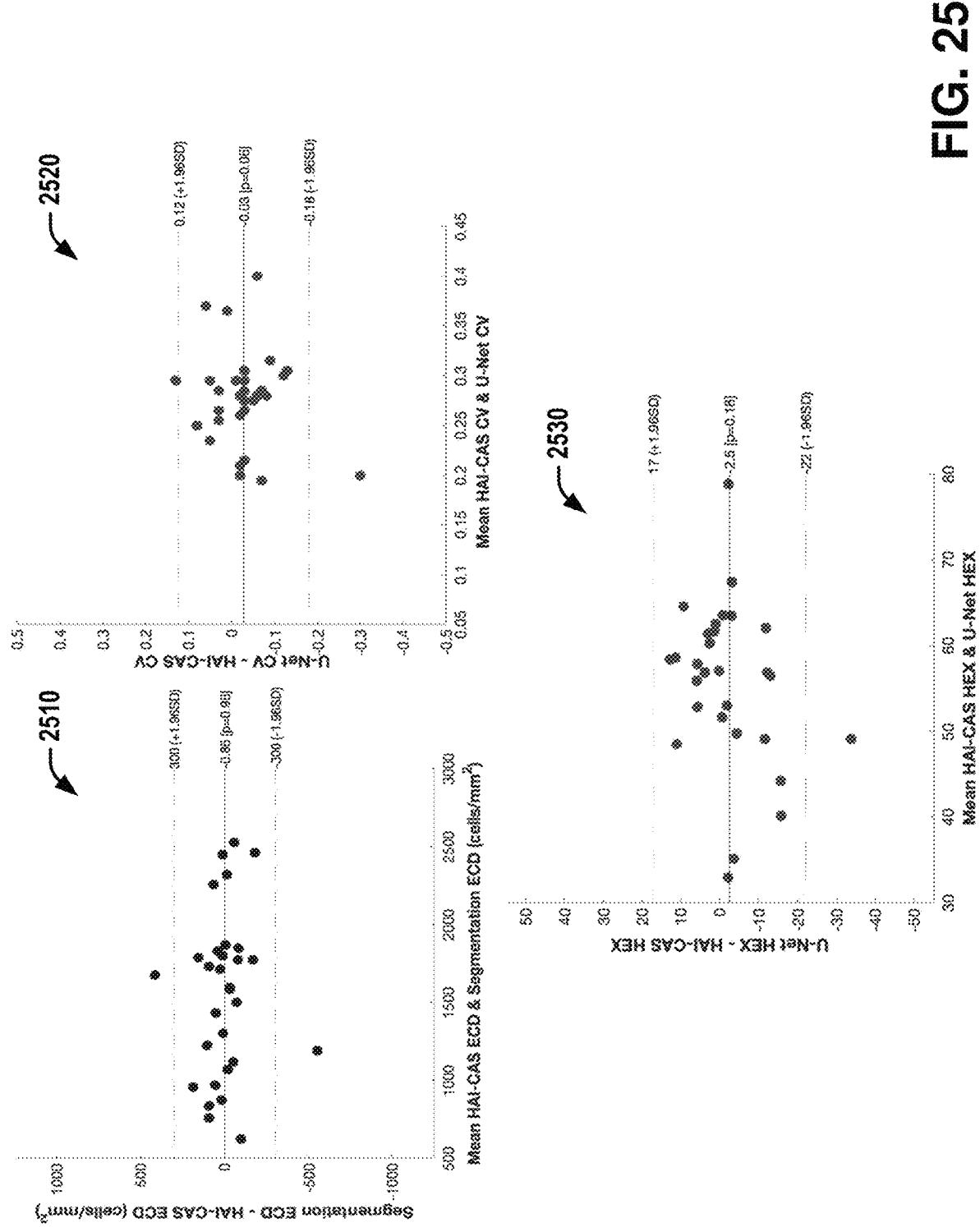
FIG. 25 illustrates Bland Altman plots for endothelial cell density (ECD), coefficient of variation (CV) of cell area, and hexagonality (HEX), in connection with various aspects discussed herein.

Referring to FIG. 25, illustrated are Bland Altman plots for ECD, CV, and HEX, in connection with various aspects discussed herein.

Figure 26:
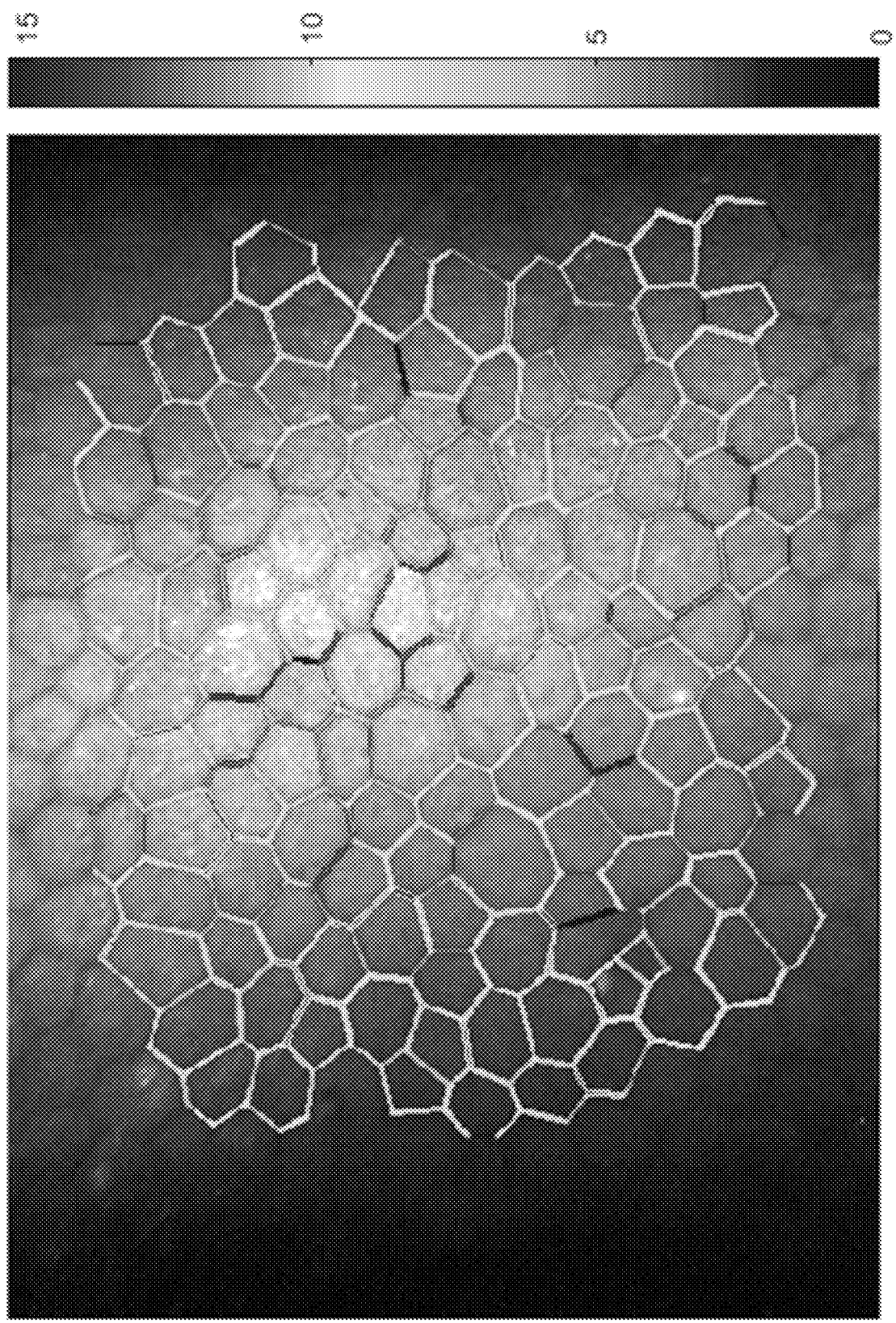
FIG. 26 illustrates a heatmap of an example EC image, showing border thickness, in connection with various aspects discussed herein.

Referring to FIG. 26, illustrated is a heatmap of an example EC image, showing border thickness, in connection with various aspects discussed herein. Border thickness was measured from EC images because it is believed that when the cornea swells, the cell borders of the endothelium will thicken.

Figure 27:
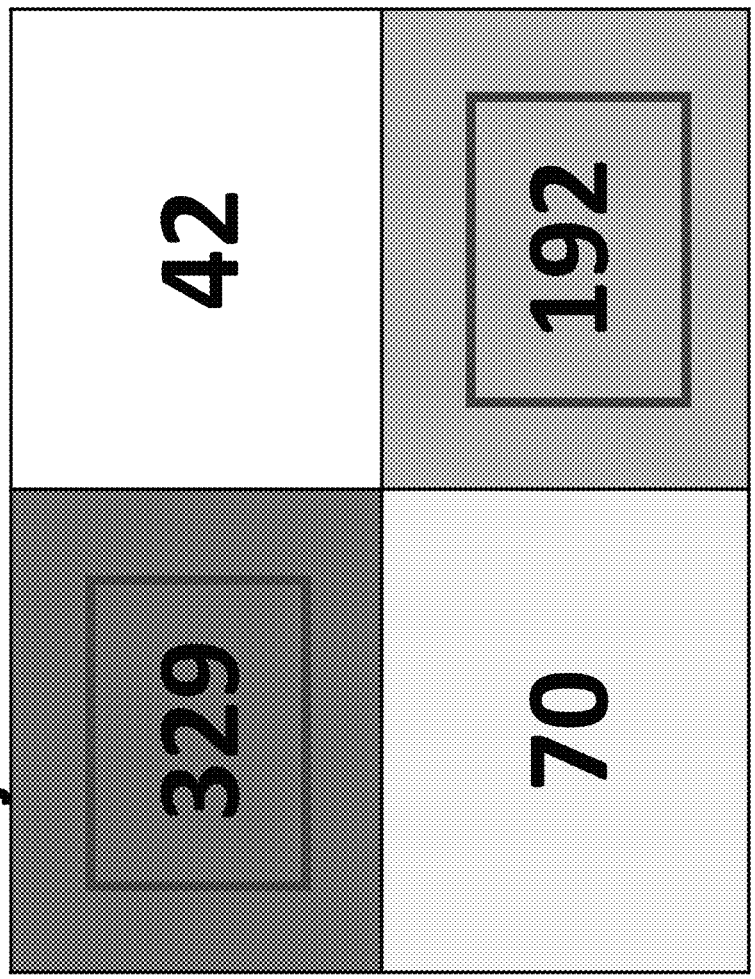
FIG. 27 illustrates a confusion matrix showing predicted and actual classification results for a machine learning classifier trained and tested on a small cohort of EC images from the Netherlands Institute of Innovative Ocular Surgery, in connection with various aspects discussed herein.

Referring to FIG. 27, illustrated is a confusion matrix showing predicted and actual classification results for a machine learning classifier of the example use case, in connection with various aspects discussed herein. A small data cohort of 28 patients with 633 EC images was used to train a random forest machine learning classifier (with 5-fold cross validation, as discussed above) to predict keratoplasty rejection. From the confusion matrix, out of 371 EC images from rejection eyes, the model accurately classified 329 images as rejection, giving a sensitivity of 0.8868, and correctly identified 192 of the 262 control images, for a specificity of 0.7328.

Once trained, the algorithm can be deployed to analyze EC images for the risk of failure or rejection. All training can be encoded in a deployed machine learning model. Various embodiments can be deployed on a stand-alone computer or distributed over the internet from a server. Additionally, as more data becomes available, learning algorithms can be trained on more data, and new model(s) created for deployment.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, 400, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing models or classifiers to generate a prognosis for keratoplasty based at least in part on features that are not perceivable by the human eye, and involve computation that cannot be practically performed in the human mind. As one example, machine learning and/or deep learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 28:
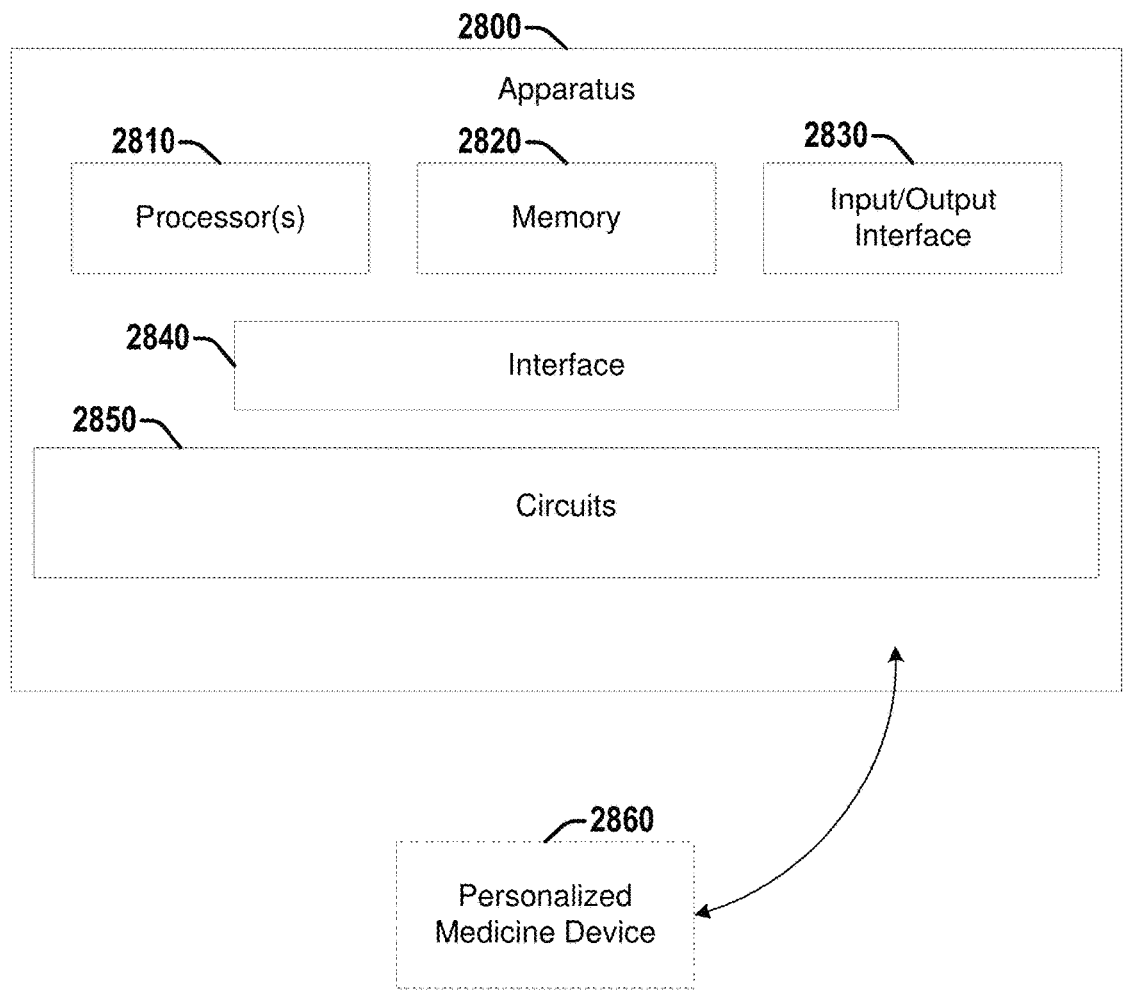
FIG. 28 illustrates a diagram of an example apparatus that can facilitate determination of a prognosis for keratoplasty from an optical image (e.g., obtained via specular or confocal microscopy) and/or training a machine learning (ML) or deep learning (DL) model to perform such determination, according to various embodiments discussed herein.

Referring to FIG. 28, illustrated is a diagram of an example apparatus 2800 that can facilitate determination of a prognosis for keratoplasty from an optical image (e.g., obtained via specular or confocal microscopy) and/or training a machine learning (ML) or deep learning (DL) model to perform such determination, according to various embodiments discussed herein. Apparatus 2800 can be configured to perform various techniques discussed herein, for example, various operations discussed in connection with sets of operations 100, 200, 300, and/or 400. Apparatus 2800 can comprise one or more processors 2810 and memory 2820. Processor(s) 2810 can, in various embodiments, comprise circuitry such as, but not limited to, one or more single-core or multi-core processors. Processor(s) 2810 can include any combination of general-purpose processors and dedicated processors (e.g., graphics processors, application processors, etc.). The processor(s) can be coupled with and/or can comprise memory (e.g., of memory 2820) or storage and can be configured to execute instructions stored in the memory 2820 or storage to enable various apparatus, applications, or operating systems to perform operations and/or methods discussed herein. Memory 2820 can be configured to store one or more digitized microscopic images (e.g., obtained via specular or confocal microscopy, etc.) of corneal endothelial cells (e.g., for training and/or prognosticating). Each of the image(s) can comprise a plurality of pixels or voxels, each pixel or voxel having an associated intensity. Memory 2820 can be further configured to store additional data involved in performing operations discussed herein, such as for determining a prognosis following keratoplasty (e.g., no adverse events vs. failure, no adverse events vs. non-rejection failure vs. rejection, etc.) from an optical microscopic image and/or training a ML or DL model to generate a prognosis for keratoplasty from an optical microscopic image, as discussed in greater detail herein.

Apparatus 2800 can also comprise an input/output (I/O) interface 2830 (e.g., associated with one or more I/O devices), a set of circuits 2850, and an interface 2840 that connects the processor(s) 2810, the memory 2820, the I/O interface 2830, and the set of circuits 2850. I/O interface 2830 can be configured to transfer data between memory 2820, processor 2810, circuits 2850, and external devices, for example, a medical imaging device (e.g., specular or confocal microscope, etc.), and/or one or more remote devices for receiving inputs and/or providing outputs to a clinician, patient, etc., such as optional personalized medicine device 2860.

The processor(s) 2810 and/or one or more circuits of the set of circuits 2850 can perform one or more acts associated with a method or set of operations discussed herein, such as set of operations 100, 200, 300, and/or 400. In various embodiments, different acts (e.g., different operations of a set of operations) can be performed by the same or different processor(s) 2810 and/or one or more circuits of the set of circuits 2850.

Apparatus 2800 can optionally further comprise personalized medicine device 2860. Apparatus 2800 can be configured to provide the keratoplasty prognosis (e.g., no adverse events vs. failure, no adverse events vs. non-rejection failure vs. rejection, etc.) for the patient, and/or other data (e.g., segmented endothelial cells, suggested interventions, etc.) to personalized medicine device 2860. Personalized medicine device 2860 may be, for example, a computer assisted diagnosis (CADx) system or other type of personalized medicine device that can be used to facilitate monitoring and/or treatment of an associated medical condition. In some embodiments, processor(s) 2810 and/or one or more circuits of the set of circuits 2850 can be further configured to control personalized medicine device 2860 to display the keratoplasty prognosis for the patient or other data on a computer monitor, a smartphone display, a tablet display, or other displays.

Examples herein can include subject matter such as an apparatus, a microscope (e.g., specular, confocal, etc.), a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for segmenting endothelial cells and/or generating a prognosis for keratoplasty, according to embodiments and examples described.

Example 1 is a non-transitory computer-readable medium storing computer-executable instructions that, when executed, cause a processor to perform operations, comprising: accessing an optical microscopy image comprising a set of corneal endothelial cells of a patient of a keratoplasty; segmenting, based at least in part on a first model, a plurality of corneal endothelial cells of the set of corneal endothelial cells; calculating one or more features based on the segmented plurality of corneal endothelial cells; and generating, via a second model trained based at least on the one or more features, a prognosis associated with the keratoplasty.

Example 2 comprises the subject matter of any variation of any of example(s) 1, wherein the first model is a convolutional neural network (CNN).

Example 3 comprises the subject matter of any variation of any of example(s) 1-2, wherein the second model is one of a Support Vector Machine (SVM) classifier, a Random Forest (RF) classifier, a Linear Discriminant Analysis (LDA) classifier, or a Quadratic Discriminant Analysis (QDA) classifier.

Example 4 comprises the subject matter of any variation of any of example(s) 1-3, wherein the one or more features comprise one or more graph features associated with the segmented plurality of corneal endothelial cells.

Example 5 comprises the subject matter of any variation of any of example(s) 1-4, wherein the one or more features comprise one or more features associated with at least one of wall thicknesses, bright pigments, or dark nuclei associated with the segmented plurality of corneal endothelial cells.

Example 6 comprises the subject matter of any variation of any of example(s) 1-5, wherein the one or more features comprise one or more of an endothelial cell density, a coefficient of variation of cell area, or a hexagonality associated with the segmented plurality of corneal endothelial cells.

Example 7 comprises the subject matter of any variation of any of example(s) 1-6, wherein the operations further comprise performing preprocessing on the optical microscopy image.

Example 8 comprises the subject matter of any variation of any of example(s) 1-7, wherein the segmenting comprises performing binarizing a probability map generated by the first model based on one of an adaptive threshold or an Otsu threshold.

Example 9 comprises the subject matter of any variation of any of example(s) 1-8, wherein the prognosis is one of a non-adverse outcome or a failure.

Example 10 comprises the subject matter of any variation of any of example(s) 1-8, wherein the prognosis is one of a non-adverse outcome, a non-rejection failure, or a rejection.

Example 11 is a non-transitory computer-readable medium storing computer-executable instructions that, when executed, cause a processor to perform operations, comprising: accessing a training set comprising a plurality of optical microscopy images, wherein each optical microscopy image of the training set comprises an associated set of corneal endothelial cells of a patient associated with that optical microscopy image, and wherein each optical microscopy image of the training set is associated with a known prognosis; for each optical microscopy image of the training set: segmenting, based at least in part on a first model, a plurality of corneal endothelial cells of the set of corneal endothelial cells of that optical microscopy image; and calculating a set of features for that optical microscopy image based on the segmented plurality of corneal endothelial cells of that optical microscopy image; and based at least on the calculated set of features for each optical microscopy image and the known prognosis for each optical microscopy image, training a second model to determine an associated prognosis for an additional optical microscopy image, based on calculating the set of features for the additional optical microscopy image based on a segmented plurality of corneal endothelial cells of the additional optical microscopy image.

Example 12 comprises the subject matter of any variation of any of example(s) 11, wherein the first model is a convolutional neural network (CNN).

Example 13 comprises the subject matter of any variation of any of example(s) 11-12, wherein the second model is one of a Support Vector Machine (SVM) classifier, a Random Forest (RF) classifier, a Linear Discriminant Analysis (LDA) classifier, or a Quadratic Discriminant Analysis (QDA) classifier.

Example 14 comprises the subject matter of any variation of any of example(s) 11-13, wherein the one or more features comprise one or more graph features associated with the segmented plurality of corneal endothelial cells.

Example 15 comprises the subject matter of any variation of any of example(s) 11-14, wherein the one or more features comprise one or more features associated with at least one of wall thicknesses, bright pigments, or dark nuclei associated with the segmented plurality of corneal endothelial cells.

Example 16 comprises the subject matter of any variation of any of example(s) 11-15, wherein the one or more features comprise one or more of an endothelial cell density, a coefficient of variation of cell area, or a hexagonality associated with the segmented plurality of corneal endothelial cells.

Example 17 comprises the subject matter of any variation of any of example(s) 11-16, wherein the operations further comprise performing preprocessing on the optical microscopy image.

Example 18 comprises the subject matter of any variation of any of example(s) 11-17, wherein the segmenting comprises performing binarizing a probability map generated by the first model based on one of an adaptive threshold or an Otsu threshold.

Example 19 comprises the subject matter of any variation of any of example(s) 11-18, wherein the prognosis is one of a non-adverse outcome or a failure.

Example 20 comprises the subject matter of any variation of any of example(s) 11-18, wherein the prognosis is one of a non-adverse outcome, a non-rejection failure, or a rejection.

Example 21 comprises the subject matter of any variation of any of example(s) 11-20, wherein the set of features are selected based on one of a minimum redundancy maximum relevance method, a Cox proportional hazards model, or a Wilcoxon rank-sum test.

Example 22 is a non-transitory computer-readable medium storing computer-executable instructions that, when executed, cause a processor to perform operations, comprising: accessing a training set comprising a plurality of optical microscopy images, wherein each optical microscopy image of the training set comprises an associated set of corneal endothelial cells of a patient associated with that optical microscopy image, and wherein each optical microscopy image of the training set is associated with a ground truth segmentation of plurality of corneal endothelial cells of the set of corneal endothelial cells of that optical microscopy image; and based at least on each optical microscopy image and the ground truth segmentation for each optical microscopy image, training a deep learning model to segment a plurality of corneal endothelial cells of a set of corneal endothelial cells of an additional optical microscopy image.

Example 23 comprises the subject matter of any variation of any of example(s) 22, wherein the deep learning model is a convolutional neural network (CNN).

Example 24 comprises the subject matter of any variation of any of example(s) 22-23, wherein the operations further comprise performing preprocessing on each optical microscopy image of the training set.

Example 25 comprises an apparatus comprising means for executing any of the described operations of examples 1-24.

Example 26 comprises a machine readable medium that stores instructions for execution by a processor to perform any of the described operations of examples 1-24.

Example 27 comprises an apparatus comprising: a memory; and one or more processors configured to: perform any of the described operations of examples 1-24.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing an optical microscopy image comprising a set of corneal endothelial cells of a patient of a keratoplasty;
    segmenting, based at least in part on a first model, a plurality of corneal endothelial cells of the set of corneal endothelial cells;
    calculating one or more features from the segmented plurality of corneal endothelial cells, wherein calculating the one or more features includes calculating bright pigments, dark nuclei, and a thickness of dark gaps between cells of the segmented plurality of corneal endothelial cells; and generating, via a second model using the one or more features, a prognosis associated with the keratoplasty at a time following the keratoplasty.

2. The non-transitory computer-readable medium of claim 1, wherein the one or more features comprise statistical measures over the optical microscopy image, the statistical measures including one or more of a skewness, a kurtosis, and a binned histogram.

3. The non-transitory computer-readable medium of claim 1, wherein the one or more features are calculated after segmenting the plurality of corneal endothelial cells.

4. The non-transitory computer-readable medium of claim 1, wherein the one or more features comprise one or more graph features associated with the segmented plurality of corneal endothelial cells, the one or more graph features describing an arrangement between the segmented plurality of corneal endothelial cells.

5. The non-transitory computer-readable medium of claim 1, wherein the one or more features comprise one or more of an endothelial cell density, a coefficient of variation of cell area, or a hexagonality associated with the segmented plurality of corneal endothelial cells.

6. The non-transitory computer-readable medium of claim 1, wherein the operations further comprise performing pre-processing on the optical microscopy image.

7. The non-transitory computer-readable medium of claim 1, wherein the segmenting comprises;
correcting illumination artifacts across an image area;
generating pixel-wise class probability maps; and
thresholding the pixel-wise class probability maps to generate a final binary segmentation map.

8. The non-transitory computer-readable medium of claim 7, wherein the thresholding is calculated within a sliding window at each pixel location, the thresholding calculating an adaptive threshold value that is equal to:

$$T=m[1+k(\sigma/\sigma_{dyn}-1)]; \text{ and}$$

wherein m is a mean intensity in a pixel neighborhood, $\sigma$ is a standard deviation in the pixel neighborhood, $\sigma_{dyn}$ is a difference between maximum and minimum standard deviations across the optical microscopy image, and k is a tunable parameter.

9. The non-transitory computer-readable medium of claim 1, wherein the operations further comprise:
receiving a segmentation result from the first model, the segmentation result having segmentation errors; and
highlighting cells within the segmentation result that are deemed to have been segmented incorrectly by the first model to a user by way of a graphical user interface (GUI), wherein the user can manually erase or edit cell boundaries corresponding to cells that have been highlighted.

10. The non-transitory computer-readable medium of claim 1, wherein the one or more features further comprise one or more graph features include an average area extracted from a Voronoi graph, an average eccentricity extracted from a cell cluster graph, or a standard deviation of an edge length extracted from a minimum spanning tree.

11. The non-transitory computer-readable medium of claim 1, wherein the one or more features further comprise hand-crafted features including irregular cell morphology, irregular distribution, cell nuclei, cellular reflectivity, and wall thickness.

12. The non-transitory computer-readable medium of claim 1, wherein calculating the dark nuclei comprises:
correcting intensity background variations and reducing noise of the segmented plurality of corneal endothelial cells; and
applyinh a conditional dilation to a threshold.

13. The non-transitory computer-readable medium of claim 1, wherein calculating the one or more features comprises:
correcting intensity background variations and reducing noise of the segmented plurality of corneal endothelial cells; and
identifying the dark nuclei and the bright pigments using the segmented plurality of corneal endothelial cells after correcting the intensity background variations and reducing the noise.

14. A non-transitory computer-readable medium storing computer-executable instructions that, when executed, cause a processor to perform operations, comprising:
accessing a training set comprising a plurality of optical microscopy images, wherein each optical microscopy image of the training set comprises an associated set of corneal endothelial cells of a patient of a keratoplasty associated with that optical microscopy image, and wherein each optical microscopy image of the training set is associated with a ground truth segmentation of a plurality of corneal endothelial cells of the set of corneal endothelial cells of that optical microscopy image;
based at least on each optical microscopy image and the ground truth segmentation for each optical microscopy image, training a deep learning model to segment the plurality of corneal endothelial cells of the set of corneal endothelial cells;
calculating one or more features from the segmented plurality of corneal endothelial cells, wherein calculating the one or more features includes calculating bright pigments, dark nuclei, and a thickness of dark gaps between cells of the segmented plurality of corneal endothelial cells; and
generating, via a second model trained based at least on the one or more features, a prognosis associated with the keratoplasty at a time following the keratoplasty.

15. The non-transitory computer-readable medium of claim 14, wherein the deep learning model is a convolutional neural network (CNN).

16. The non-transitory computer-readable medium of claim 14, wherein the operations further comprise performing preprocessing on each optical microscopy image of the training set.

17. A method, comprising:
accessing an optical microscopy image comprising corneal endothelial cells of a patient of a keratoplasty;
segmenting, based at least in part on a first model, a plurality of corneal endothelial cells of the optical microscopy image;
receiving a segmentation result from the first model, the segmentation result having segmentation errors; and
highlighting cells within the segmentation result that are deemed to have been segmented incorrectly by the first model to a user, wherein the user can manually erase or edit cell boundaries corresponding to cells that have been highlighted;
calculating one or more features from the segmented plurality of corneal endothelial cells; and generating, via a second model using the one or more features, a prognosis associated with the keratoplasty at a time following the keratoplasty.

18. The method of claim 17, wherein the segmenting includes:
   correcting illumination artifacts across an image area by generating a low-pass background image using a Gaussian blur and dividing an original image with the low-pass background image;
   generating pixel-wise class probability maps; and
   performing thresholding and morphological processing operations on the pixel-wise class probability maps to generate a final binary segmentation map.

19. The method of claim 17, wherein the one or more features comprise one or more graph features associated with the segmented plurality of corneal endothelial cells, the one or more graph features describing an arrangement between the segmented plurality of corneal endothelial cells.

20. The method of claim 17, wherein the one or more features comprise one or more local or global graph features associated with the segmented plurality of corneal endothelial cells.

21. The method of claim 20,
   wherein the one or more features further comprise endothelial cell density (ECD), coefficient of variation (CV) of cell area, and hexagonality (HEX); and
   wherein the CV of cell area is determined by:
      calculating an individual cell area for each of the plurality of corneal endothelial cells, the individual cell areas respectively including a cell border;
      calculating a standard deviation and a mean of the individual cell areas; and
      determining the CV of the individual cell area as a ratio of the standard deviation and the mean of individual cell areas.

22. The method of claim 17, wherein calculating the one or more features includes calculating dark nuclei, bright pigments, and a thickness of dark gaps between cells of the segmented plurality of corneal endothelial cells.

23. The method of claim 22, wherein calculating the one or more features associated with dark nuclei comprises:
   correcting intensity background variations and reducing noise of the segmented plurality of corneal endothelial cells; and
   applying a conditional dilation to a threshold.

24. The method of claim 17, wherein the one or more features further comprise one or more graph features including an average area extracted from a Voronoi graph, an average eccentricity extracted from a cell cluster graph, and a standard deviation of an edge length extracted from a minimum spanning tree.

* * * * *